(12) United States Patent
Izumi

(10) Patent No.: US 8,622,921 B2
(45) Date of Patent: Jan. 7, 2014

(54) SLEEP EVALUATION DEVICE AND SLEEP EVALUATION METHOD THEREFOR

(75) Inventor: Shuichi Izumi, Itabashi-Ku (JP)

(73) Assignee: Tanita Corporation, Itabashi-Ku, Tokyo (JP)

( * ) Notice: Subject to any disclaimer, the term of this patent is extended or adjusted under 35 U.S.C. 154(b) by 1399 days.

(21) Appl. No.: 12/330,883

(22) Filed: Dec. 9, 2008

(65) Prior Publication Data

US 2009/0171165 A1   Jul. 2, 2009

(30) Foreign Application Priority Data

Dec. 28, 2007 (JP) .................................. 2007-338993

(51) Int. Cl.
*A61B 5/08* (2006.01)

(52) U.S. Cl.
USPC .......................................................... 600/534

(58) Field of Classification Search
None
See application file for complete search history.

(56) References Cited

U.S. PATENT DOCUMENTS

| 4,306,567 | A | * | 12/1981 | Krasner | 600/484 |
| 5,479,939 | A | | 1/1996 | Ogino | |
| 5,724,990 | A | | 3/1998 | Ogino | |
| 5,902,255 | A | | 5/1999 | Ogino | |
| 2006/0009704 | A1 | * | 1/2006 | Okada et al. | 600/529 |
| 2007/0118054 | A1 | | 5/2007 | Pinhas et al. | |
| 2008/0269625 | A1 | * | 10/2008 | Halperin et al. | 600/508 |
| 2008/0306351 | A1 | | 12/2008 | Izumi | |

FOREIGN PATENT DOCUMENTS

| JP | H03-258246 A | 11/1991 |
| JP | H04-28352 A | 1/1992 |
| JP | H05-95934 A | 4/1993 |
| JP | H07-204166 A | 8/1995 |
| JP | 2000-000214 A | 1/2000 |
| JP | 2006-20810 A | 1/2006 |
| JP | 2006-271474 A | 10/2006 |
| JP | 2008-301951 A | 12/2008 |

OTHER PUBLICATIONS

Extended European Search Report issued in EP 08 02 1561.9, Apr. 23, 2009, EPO, Munich, DE.
Official Action dated Oct. 29, 2010, issued by the Japanese Patent Office in corresponding Japanese patent application No. 2007-338993, and English language translation of the Official Action.

* cited by examiner

*Primary Examiner* — Anna Skibinsky
(74) *Attorney, Agent, or Firm* — Buchanan Ingersoll & Rooney PC

(57) ABSTRACT

A sleep evaluation device (1) has a sensor unit (2) that constantly detects body movements of a human subject on bedding, and has a determiner that, based on results of detection, determines a sleep state and an aroused state of the human subject. The determiner quantifies results of detection of the sensor unit into N number of body movement data (where, N is a positive integral number satisfying $N \geq 2$) and obtains, based on G number of standard deviations for each of G groups (in which G is an integral number satisfying $2 \leq G < N$) dividing N number of body movement data and for each body movement data and gs ($gs < G$) number of standard deviations selected therefrom, L number of average value of standard deviations (where L is an integral number satisfying $2 \leq L \leq G$). The determination of a sleep state and an aroused state of the human subject is based on G number of standard deviations and L number of average values of standard deviations.

7 Claims, 19 Drawing Sheets

FIG. 10

| | OUT-OF-BED | ROLLING-OVER |
|---|---|---|
| Stage[0] | 1 → | 1 |
| Stage[1] | 0 | 0 |
| Stage[2] | 1 → | 1 |
| Stage[3] | 0 | 0 |
| Stage[4] | 0 | 0 |
| Stage[5] | 0 | 0 |
| Stage[6] | 0 | 0 |
| Stage[7] | 0 | 1 |
| Stage[8] | 0 | 0 |
| Hensa[9] | 1 → | 1 |
| | BASED ON Hensa[x] | BASED ON Hensa[x] |

FIG. 13

| MOVEMENTS OF HUMAN SUBJECTS | Move | | Value | Baseline + Value | HenAv[x] THAT MAKES DETERMINATION OF STEP S88 OF FIG. 11 "YES" |
|---|---|---|---|---|---|
| EXTREMELY ACTIVE | EQUAL TO OR GREATER THAN H2 | | J1 | SMALL | SMALL |
| INTERMEDIATE | LESS THAN H2, EQUAL TO OR GREATER THAN H3 | | J2 | MEDIUM | MEDIUM |
| QUIET | LESS THAN H3, EQUAL TO OR GREATER THAN H1 | | J3 | LARGE | LARGE |
| EXTREMELY QUIET | LESS THAN H1 | | | | |

※ H2 > H3 > H1

※ J3 > J2 > J1

SLEEP EVALUATION DEVICE AND SLEEP EVALUATION METHOD THEREFOR

FIELD OF THE INVENTION

The present invention relates to a device for evaluating sleep by determining whether or not a subject is asleep and the depth of sleep (for example, sleep duration and quality of sleep) and to a method therefor.

DESCRIPTION OF RELATED ART

Conventionally, devices have been provided for measuring biometric information of a human body during sleep or for executing a certain type of evaluation based on the measured biometric information (hereinafter referred to collectively as "sleep evaluation devices"). According to these sleep evaluation devices, information such as how many hours of substantial sleep were obtained since a human subject went to bed until the subject woke up can be confirmed by specific values. Furthermore, there is also a device that has a function of issuing a warning to an attendant or the like, in a case in which an abnormality is observed in the biometric information during sleep, so as to prompt the attendant or the like to take appropriate measures.

Japanese Patent Application Laid-Open Publication No. 2000-000214 (hereinafter referred to as JP 2000-000214) is known as an example of such a sleep evaluation device.

The technique disclosed in JP 2000-000214 has "a body movement detection means . . . positioned under a test subject's body" and "a signal extraction means to extract at least one signal from an output signal of the body movement detection means among a signal of a heart rate, a respiration rate, rolling-over frequency, and snoring", to "detect this test subject's body data" from the signal extracted by the signal extraction means (quoted from Claim 1 of JP 2000-000214).

In JP 2000-000214, "an air mat 11" is used as the body movement detection means (refer to Sections [0018], or [0016] and Claim 4, etc.). It is argued in the description that, since there is no need to provide "a band at a wrist, an ankle, a finger, and an arm" (Section 0005) with use of the air mat, an object of "collecting physical data" "without placing mental and physical burden" on a test subject (Sections [0010] and [0031]) can be achieved. There is little doubt that such an effect can be attained in comparison to a case in which the "band" is provided.

The "signal extraction means", however, is essential to the invention in the technique described in JP 2000-000214. The signal extraction means can be considered as a means for "shaping" "body data" (Section [0021]) as described in JP 2000-000214 or a type of intermediate means for carrying out the shaping of body data, but "extracting at least one signal from among a signal of a heart rate, a respiration rate, rolling-over frequency, and snoring" is not necessarily very easy. Although JP 2000-000214 says that "since these body movement signals are characterized by each of frequency, amplitude, etc., there are no great difficulties in extraction" (Section 0025), a method for carrying out the extraction is not mentioned at all.

Even if the argument described in JP 2000-000214 were accepted, the technique would still require "the signal extraction means" as an intermediate means, which in turn results in increased cost of the sleep evaluation device. Furthermore, if the signal extraction and shaping as described above is assumed, it would be possible to accurately understand human sleep states to a certain degree. The use of "the signal extraction means", however, could be sometimes "excessive" in a case in which such a strict analysis of the sleep is not required, for example, in a case in which only two types of states, a sleep state or an aroused state, should be determined. Moreover, even if the signal extraction is performed, there is no guarantee, as described above, that a signal separation would be obtained through the signal extraction very easily. Thus, there is some doubt whether it is really possible to obtain performance (how much it contributes to the accurate understanding of sleep states) that is worth the cost of providing the signal extraction means.

Thus, the question is how to evaluate a human's sleep states as accurately as possible at low cost and using an easy method based on body movement data having relatively monotonic characteristics in a sense in which the body data is obtained as a certain data string in a time line.

SUMMARY OF THE INVENTION

The present invention has been considered in view of the above and has as an object to provide a sleep evaluation device for solving all or a part of the above described problems, and to provide a sleep evaluation method therefor.

To solve the above problem, a sleep evaluation device according to the present invention has a body movement detector that constantly detects body movements of a human subject lying on bedding, and a determiner that determines, based on results of the detection of the body movement detector, at least whether the human subject is in a sleep state or is in an aroused state. The determiner 1) quantifies, at a predetermined time interval, the results of the detection of the body movement detector as N number of body movement data, in which N is a positive integral number satisfying N≥2, 2) obtains G number of standard deviations for each of G groups dividing the N number of body movement data and for each body movement data included in each group, in which the G is an integral number satisfying 2≤G<N, 3) obtains L number of average values of standard deviations on the basis of gs number of standard deviations (gs<G) that have been selected from the G number of standard deviations, in which L is an integral number satisfying 2≤L≤G, and 4) determines, on the basis of the G number of standard deviations and the L number of average values of standard deviations, whether the human subject is in a sleep state or is in an aroused state.

According to the present invention, since a result of detection by the body movement detector is "quantified" "at a predetermined time interval", "the body movement data" output is obtained as chronological data.

The "standard deviation" represents, for each of G groups, a degree of variation in the body movement data that is chronological data. The "average value of standard deviations" is the average of the "standard deviations" and therefore represents a degree of variation in the body movement data over a period longer than a period corresponding to the "standard deviation" (furthermore after leveling the standard deviations to a certain degree).

Thus, since the present invention uses the "standard deviations" and the "average value of standard deviations", i.e., data obtained basically by carrying out addition, subtraction, multiplication, and division on the raw data, no complicated configuration and processing is particularly required. In spite of such ease, the "standard deviation" and "the average value of standard deviation" are different in characteristics in that the "standard deviation" appropriately represents changes in body movement of a human subject in a relatively short period of time, and furthermore, "the average value of standard deviations" appropriately represents changes in body movement in a relatively long period of time (cyclic changes can be cancelled, in particular). Using the difference in the characteristics, the understanding of sleep states of a human subject can be performed properly to a certain degree.

In summary, according to the present invention, the determination of sleep states of a human subject is possible at low cost and using an easy method, at a degree of accuracy that is as high as possible.

It is to be noted that in the present invention, a time interval indicated by the word, "constantly", may be considered as being the same as "at predetermined time intervals" according to the present invention. Preferably, however, the former is shorter than the latter. In this case, "body movement data" can be preferably obtained as digital data by performing a predetermined sampling process on "results of detection" that are analog signals.

In the sleep evaluation device of the present invention, the determiner may 1) obtain the L number of average values on the basis of consecutive gs number of standard deviations (gs<G), from among the G number of standard deviations, 2) obtain, as a baseline value, from among the L number of average values of standard deviations, the average value of all the pth average values of standard deviations that satisfy a condition that an absolute value of a difference between the pth average value of standard deviations and (p+1)th average value of standard deviations is equal to or less than a predetermined value, in which p is an integral number satisfying p≤L−1, and 3) determine, based on the baseline value, whether the human subject is in a sleep state or is in an aroused state.

According to this mode, the "baseline value" is obtained. In a case in which the average value of standard deviations is expressed as HenAv[x] (where, x is a number), the baseline value is the average value of all HenAv[p]s that satisfy ABS [HenAv[p]−HenAv[p+1]]≤A, where "ABS" means obtaining the absolute value inside the brackets "[ ]", and A represents the predetermined value. Such a "baseline value" indicates the average value of all HenAv[p]s in a case in which the body movement of a human subject remains in a stable state to a certain degree with reference to A.

According to this mode, furthermore, if such a "baseline value" as described above is repeatedly obtained, the sleep state of a human subject can be understood based on the average value of all HenAv[p]s in a case in which the body movement of a human subject remains in a stable state to a certain degree with reference to A. In other words, the sleep state of a human subject is understood by assuming that a period that is in a relatively stable period from among periods corresponding to the body movements of a human subject based on the observation performed over a relatively long period of time is a basic line (i.e., "baseline") of the human subject.

As a result, for example, as the degree of deviation from the "baseline value" of body movement data actually observed is greater, it can be more easily determined that the human subject is awake. Thus, the determination of sleep states of the human subject can be more accurately performed.

Thus, according to the present mode, introducing the concept of the "baseline value" has enabled the more accurate determination of the sleep states of a human subject.

It is to be noted that, in the present mode, it is presumed that L number of average values of standard deviations are numbered (i.e., there are "the pth", or "the (p+1)th such value). The numbers are preferably assigned based on a time of acquiring the "body movement data" included in the group on the basis of which body movement data each of the L number of average values of standard deviations was calculated.

For example, the L1-th and the L2-th average values of standard deviations can be determined respectively as "the pth" and "the (p+1)th" in a case in which the L1-th average value of standard deviations of the L number of average values of standard deviations is the average value of the standard deviation corresponding to each of the G1-th, G2-th, . . . , G10-th groups and in which a point in time at which the earliest body movement data of plural pieces of body movement data included in each group was acquired is T1, whereas in a case in which the L2-th average value of standard deviations is the average value of the standard deviations corresponding to each of the G11-th, G12-th, . . . , G20-th groups and in which a time at which the earliest body movement data of plural pieces of body movement data included in each group was acquired is T2, and in which T2>T1 (i.e., T2 is a time that is later than T1) is satisfied.

As a preferred embodiment, the determiner may obtain the L number of average values of standard deviations as a moving average value of the gs number of standard deviations.

According to such a configuration, the L number of average values of standard deviations can be appropriately determined. In other words, given that individual average values of standard deviations are the moving average value of gs number of standard deviations, the above-described leveling or the cancellation of cyclic changes (can be referred to in particular as "smoothing" as long as the concept of "the moving average value" is introduced), can be more appropriately achieved by determining the value of gs properly. Thus, according to this mode, the significance is enhanced of using "the average value of standard deviations" as an index indicating changes in body movements in a relatively long period of time.

On the other hand, accordingly, the baseline value can be more appropriately determined according to this mode.

Therefore, according to this mode, the above-described effects can be more effectively attained.

It is to be noted that the "moving average value" as used here includes, for example, a case in which the pth average value of standard deviations is the average value of standard deviations corresponding to the pth, (p−1)th, and (p−2)th groups, and the (p+1)th average value of standard deviations is the average value of standard deviations corresponding to the (p+1)th, pth, and (p−1)th groups. In the following description of embodiments, description will also be given of another example included in the "moving average value" of this mode.

Furthermore, in the sleep evaluation device of the present invention, the determiner determines, in a case in which any one of the G number of standard deviations falls below a predetermined value E, that the human subject was in an aroused state at a point in time at which a result of detection was obtained, on the basis of which result of the detection body movement data was obtained and on the basis of which body movement data the standard deviation that has fallen below the predetermined value E was calculated.

According to this mode, a particular case of the aroused state can be detected in which a human subject is no longer in bed, by properly setting the predetermined value E to a relatively low value.

Furthermore, in the sleep evaluation device of the present invention, the determiner may determine, in a case in which, from among the G number of standard deviations, a (q+1)th standard deviation is greater than a value obtained by adding a predetermined value F1 to a qth standard deviation, that the human subject was in an aroused state at a point in time at which a result of detection was obtained, on the basis of which result of detection body movement data was obtained and on the basis of which body movement data the (q+1)th standard deviation was calculated, in which q is an integer satisfying q≤G−1.

According to this mode, a point in time at which a human subject transitions to an aroused state can be appropriately determined if the predetermined value F1 is set appropriately.

It is to be noted that the same idea used in numbering L number of average values of standard deviations is preferably used for assigning the qth, or the (q+1)th numbers (i.e., the chronological order of body movement data on the basis of which the calculation was made for each of G groups).

Furthermore, in the sleep evaluation device of the present invention, the determiner may determine, in a case in which any one of the G number of standard deviations is greater than a predetermined value F2, that the human subject was in an aroused state at a point in time at which a result of detection was obtained, on the basis of which a result of detection of the body movement data was obtained and on the basis of which body movement data the standard deviation was calculated.

According to this mode, a point in time at which a human subject transitions to an aroused state can be appropriately determined if the predetermined value F2 is properly set.

Furthermore, in the sleep evaluation device of the present invention, the determiner may obtain a standard deviation of the G number of standard deviations as an overall standard deviation, obtain an index showing the quantity of body movements of the human subject by subtracting the baseline value from the average value of G number of standard deviations and by dividing a resulting value of the subtraction by the overall standard deviation, and determine a point in time at which a transition from a sleep state to an aroused state has taken place on the basis of the index showing the quantity of body movements of the human subject.

According to this mode, a preferable example of the baseline value is provided. That is, according to this mode, in a case in which the G number of standard deviations is AveHensa and the overall standard deviation is HenStd, an index, Move, indicating the frequency of movements of a human subject is obtained as, Move=(AveHensa−(baseline value))/HenStd Since Move can be considered as indicating the frequency of movements of a human subject in the literal meaning, the transition from a sleep state to an aroused state of a human subject can be appropriately determined by, for example, comparing values between a standard value suitably set on the basis of Move and each of G number of standard deviations.

Furthermore, in the sleep evaluation device of the present invention, the body movement detector may include a mattress containing a predetermined fluid and detect body movements of the human subject depending on changes in pressure of the fluid.

According to this mode, the body movement detector can detect body movements of a human subject without tethering a body of the human subject or a portion of the body. Thus, the sleep evaluation device does not place an excessive burden on a human subject, but nevertheless, the sleep states of the human subject can be accurately determined in the present invention or in various modes of the present invention.

Thus, according to the present mode, the two effects can be simultaneously attained.

Furthermore, to solve the above problem, the present invention provides a sleep evaluation method including: obtaining N number of body movement data by quantifying, at a predetermined time interval, body movements of a human subject lying on bedding, in which N is a positive integral number: obtaining G number of standard deviations for each of G groups dividing the N number of body movement data and for each body movement data included in each group, in which the G is an integral number satisfying 2≤G<N; obtaining L number of average values of standard deviations on the basis of gs standard deviations (gs<G) that have been selected from the G number of standard deviations, in which L is an integral number satisfying 2≤L≤G; and determining, on the basis of the G number of standard deviations and the L number of average values of standard deviations, whether the human subject is in a sleep state or is in an aroused state.

According to the present invention, substantially the same effects are attainable as the above-described effects that are attainable by the sleep evaluation device according to the present invention.

BRIEF DESCRIPTION OF THE DRAWINGS

FIG. 10 is an explanatory diagram showing specific values of Stage[x]s that have been set as a result of the processes of FIGS. 8 and 9.

FIG. 13 is an explanatory diagram for visually understanding relationships between parameters H1 to H3 and J1 to J3, and Move shown in FIG. 11.

DETAILED DESCRIPTION OF PREFERRED EMBODIMENTS

In the following, a description will be given of an embodiment according to the present invention with reference to FIG. 1 and subsequent figures. It is to be noted that, in the present embodiment, in each of the figures, proportional sizes of units sometimes differ from the actual proportions.

Figure 1:
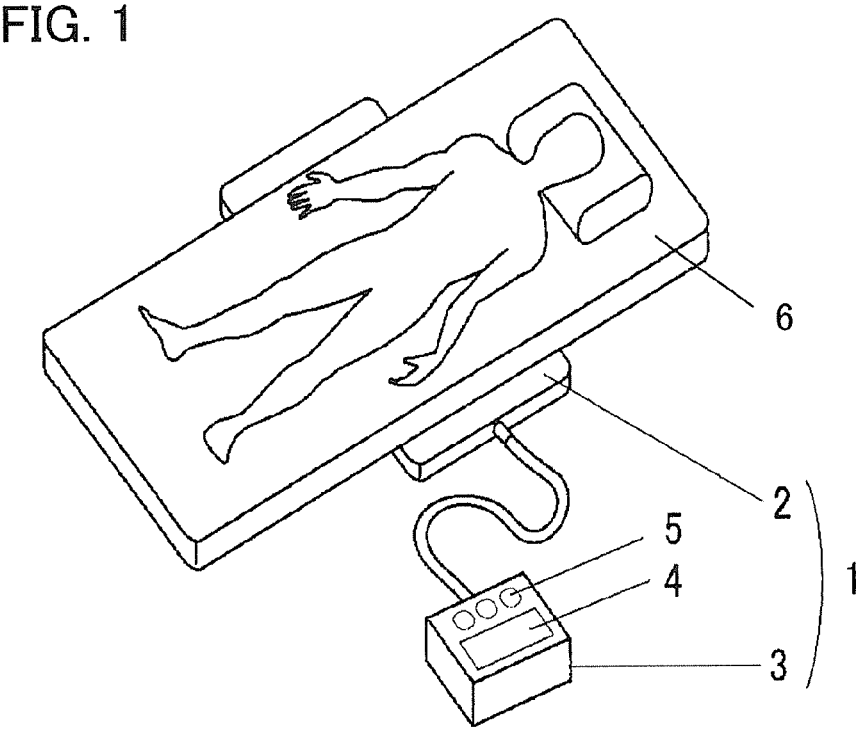
FIG. 1 is a perspective view of a sleep evaluation device according to an embodiment of the present invention, the view showing a state in which the device is being used.
Figure 2:
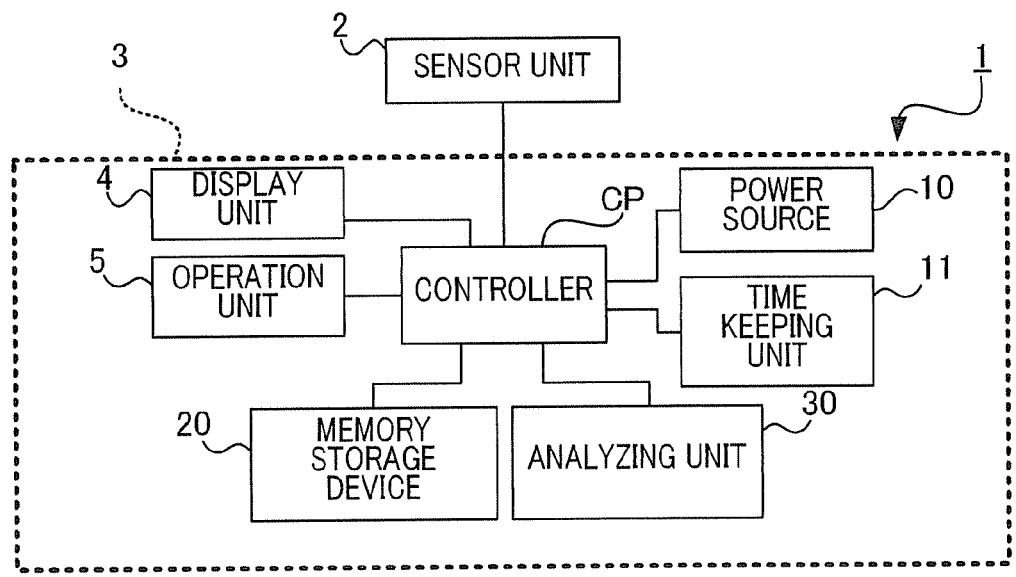
FIG. 2 is an electrical block diagram of the sleep evaluation device of FIG. 1.

FIGS. 1 and 2 will be first referred to, to describe a configuration of a sleep evaluation device. FIG. 1 is a block diagram showing an external view of sleep evaluation device 1 when the device is being used. FIG. 2 is a block diagram showing a configuration of sleep evaluation device 1.

In FIG. 1, sleep evaluation device 1 has a sensor unit 2 for detecting biometric signals of a human subject lying on the bedding and a control console 3 that is connected to sensor unit 2 and that determines a sleep state and evaluates the quality of the sleep. Control console 3 includes a display unit 4 for displaying the result of the determination of the sleep stages and also for displaying guidance such as showing evaluation indices of the sleep. Control console 3 also includes an operation unit 5 for performing operations such as power-on or power-off operations and measurement-start or measurement-ending operations.

Sensor unit 2 is, for example, capable of detecting, through a microphone (for example, a condenser microphone), variations in the pressure on a mattress 6 in which an incompressible fluid is sealed. As shown in the figure, the mattress is spread under the bedding, so that sensor unit 2 detects biometric signals including respiration signals or the changes in posture of a human subject who is lying on the bedding.

As shown in FIG. 1, sleep evaluation device 1 according to the present embodiment, there is no need to tether the body of a human subject when the measurements are being performed. This is because, as described above, the body movements of a human subject can be detected simply by placing sensor unit 2 under the bedding.

Furthermore, control console 3 is provided with, as shown in FIG. 2, a power source 10, a time keeping unit 11, a controller CP, a memory storage device 20 and an analyzing unit 30, in addition to the above described display unit 4 and operation unit 5, among which a unit that is central to the device is the controller CP. Each of the above elements is thus connected to the controller CP, so is sensor unit 2.

The controller CP is provided with an AD (analog to digital) converter for converting input signals received from sensor unit 2 into digital signals, a CPU (Central Process Unit), RAM (Random Access Memory), ROM (Read Only Memory), and other elements that are necessary (not shown).

The controller CP performs overall control so that sleep evaluation device 1 according to the present embodiment operates in harmony overall.

Power source 10 supplies electric power to sleep evaluation device 1 of the present embodiment. Furthermore, time keeping unit 11 recognizes a current time for supply to the controller CP.

Analyzing unit 30, based on changes in postures of a human subject detected by sensor unit 2 and information of a current time measured by time keeping unit 11, determines or judges the chronological changes in sleep states and the quality of sleep through calculation, analysis, and evaluation.

Memory storage device 20 stores results of the determination by the above analyzing unit 30. Alternatively, memory storage device 20, when necessary, stores intermediate results, intermediate achievement information, and the like obtained during the calculation in analyzing unit 30, and stores other various types of information and programs required for the operation of sleep evaluation device 1.

"A determiner" according to the present invention includes at least the controller CP, analyzing unit 30, and memory storage device 20 of the present embodiment.

In the following, description will be given of an operation of sleep evaluation device 1 that has the above configuration, with reference to FIGS. 3 to 22. It is to be noted that the above controller CP takes the main, leading role in various types of operations, calculations, and processes, which will be described below, unless otherwise indicated.

Figure 3:
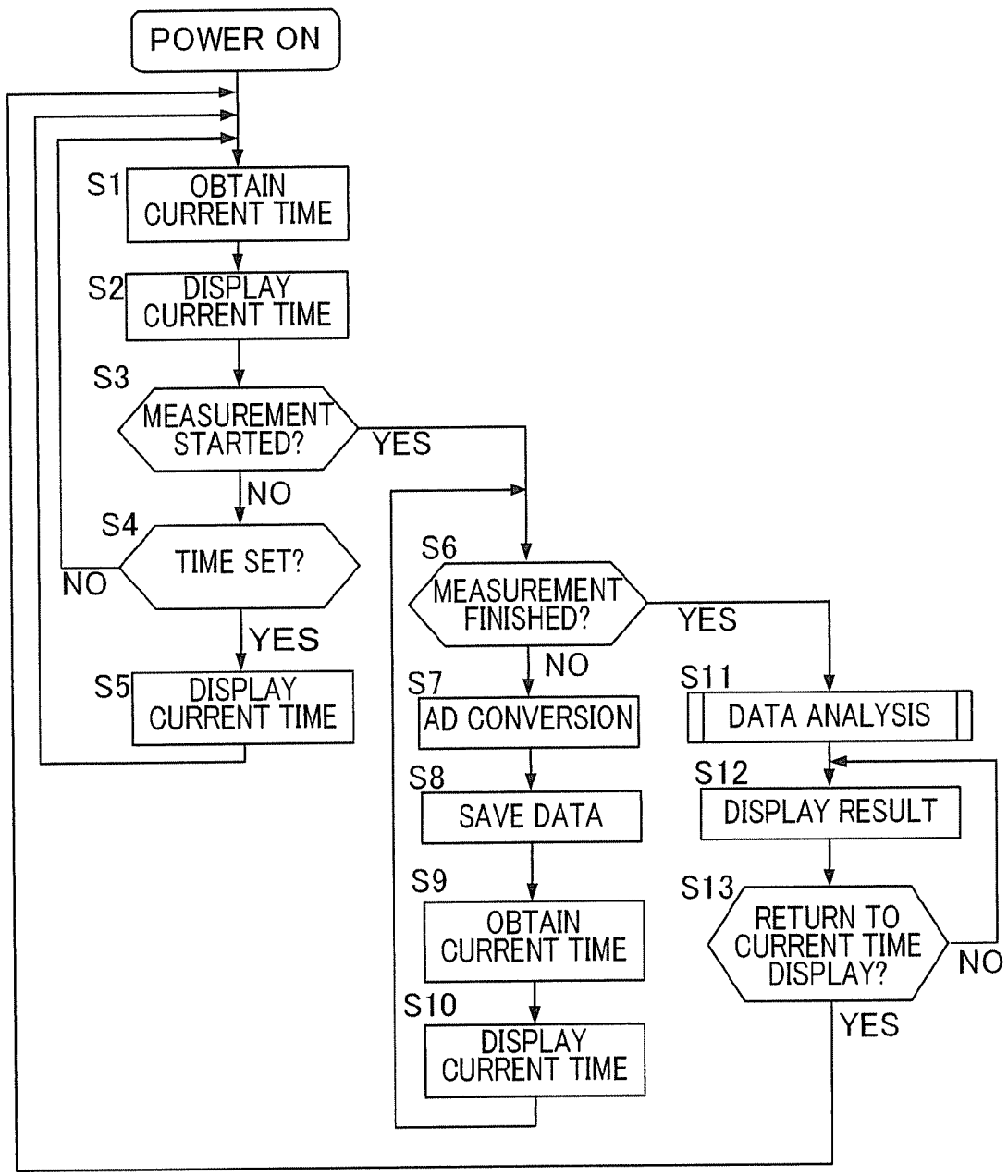
FIG. 3 is a main flowchart for using the sleep evaluation device of FIG. 1.

In a case in which the power source button in operation unit 5 of sleep evaluation device 1 is first pressed by a user, and power source 10 is turned ON, the controller CP obtains a current time (Step S1 in FIG. 3), to display the obtained current time on display unit 4 (Step S2 in FIG. 3).

Subsequently, the controller CP determines whether an instruction for starting the measurement has been made (Step S3 in FIG. 3). The instruction is issued, for example, based on a pressing operation by a user of a measurement start button of operation unit 5, or alternatively is automatically issued in a case in which it has reached a certain time. Furthermore, the term "measurement" as used here means measuring chronological changes in the body movements of a human subject detected by sensor unit 2.

In a case in which no measurement start instruction has been issued, sleep evaluation device 1 according to the present embodiment basically repeats the above current time acquiring process and the display process thereafter (refer to Step S4: NO in FIG. 3). However, in a case in which another current time is set by a user by using operation unit 5 (Step S4: YES in FIG. 3) when the repeat process is being executed, a process of displaying the set time (Step S5 in FIG. 3) is inserted.

On the other hand, in a case in which there has been a measurement start instruction, the controller CP escapes from the repeat process to proceed to another process. That is, it is first determined whether the measurement has finished (Step S6 in FIG. 3). In a case in which it is determined that the measurement is not finished (Step S6: NO in FIG. 3), the controller CP executes an AD conversion on a signal scanned through sensor unit 2 (Step S7 in FIG. 3), and digital data obtained through the AD conversion process is stored in memory storage device 20 as body movement data (Step S8 in FIG. 3).

Figure 4:
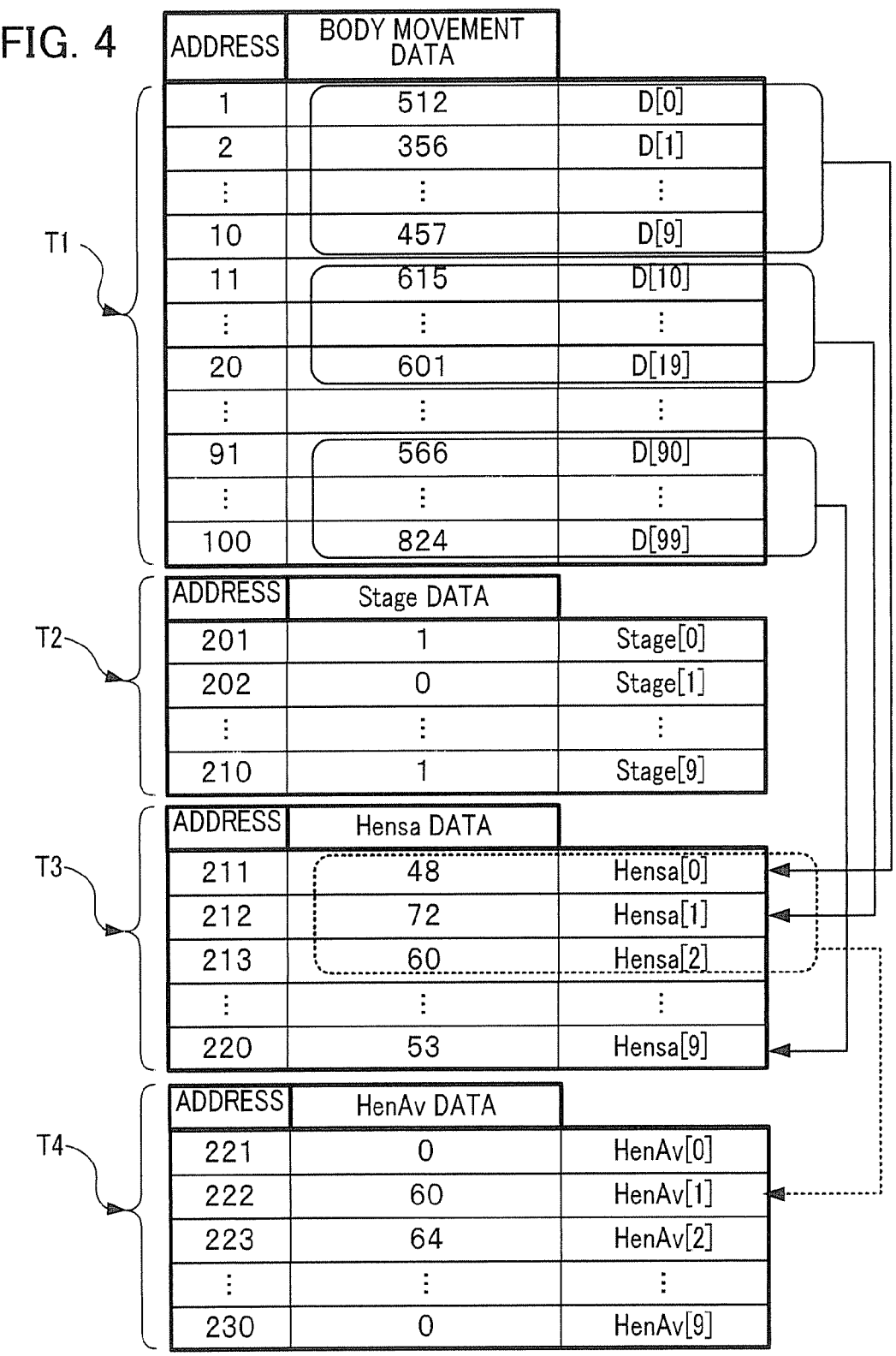
FIG. 4 is an explanatory diagram showing configuration examples of each specific value of D[x], Stage[x], Hensa[x], and HenAv[x] configured in a storage device of FIG. 2.

As a result of performing the above sequential process, a data table T1 as shown as an example in FIG. 4 is configured in memory storage device 20. The data table T1 sequentially accepts a write operation of body movement data corresponding to address numbers 1 to 100 of memory storage device 20. As shown in the figure, each body movement piece of data 512, 356, ..., 457, 615, 601, ..., 824 has been written in an address. It is to be noted that D[0], D[1], ..., D[99] are variable identifiers, and that the number of pieces of data for body movements being 100 is merely an example.

The controller CP obtains (Step S9 in FIG. 3) and displays (Step S10 in FIG. 3) a current time in parallel while constructing such a data table T1.

In Step S6 in FIG. 3, in a case in which it is determined that the measurement is finished, i.e., in a case in which the construction of the data table T1 is completed (Step S6: YES in FIG. 3), the body movement data in the data table T1 is analyzed (Step S11 in FIG. 3). This data analysis process will be described in detail later in the description.

In a case in which this data analysis is completed, the controller CP displays a result of the analysis (Step S12 in FIG. 3). It is then determined whether to return to the display process of a current time, and when this determination is affirmative, the controller CP returns to the repeat process (from Step S13: YES to Step S1 in FIG. 3). It is to be noted that the determination of Step S13 can also be understood as, for example, the determination as to whether the results of the analysis are displayed long enough for a user to view it. This determination can be confirmed when the controller CP determines that a certain period has elapsed or when it is so indicated by the user.

Description will be next given of the details of a data analysis process in Step S11 in FIG. 3.

Figure 5:
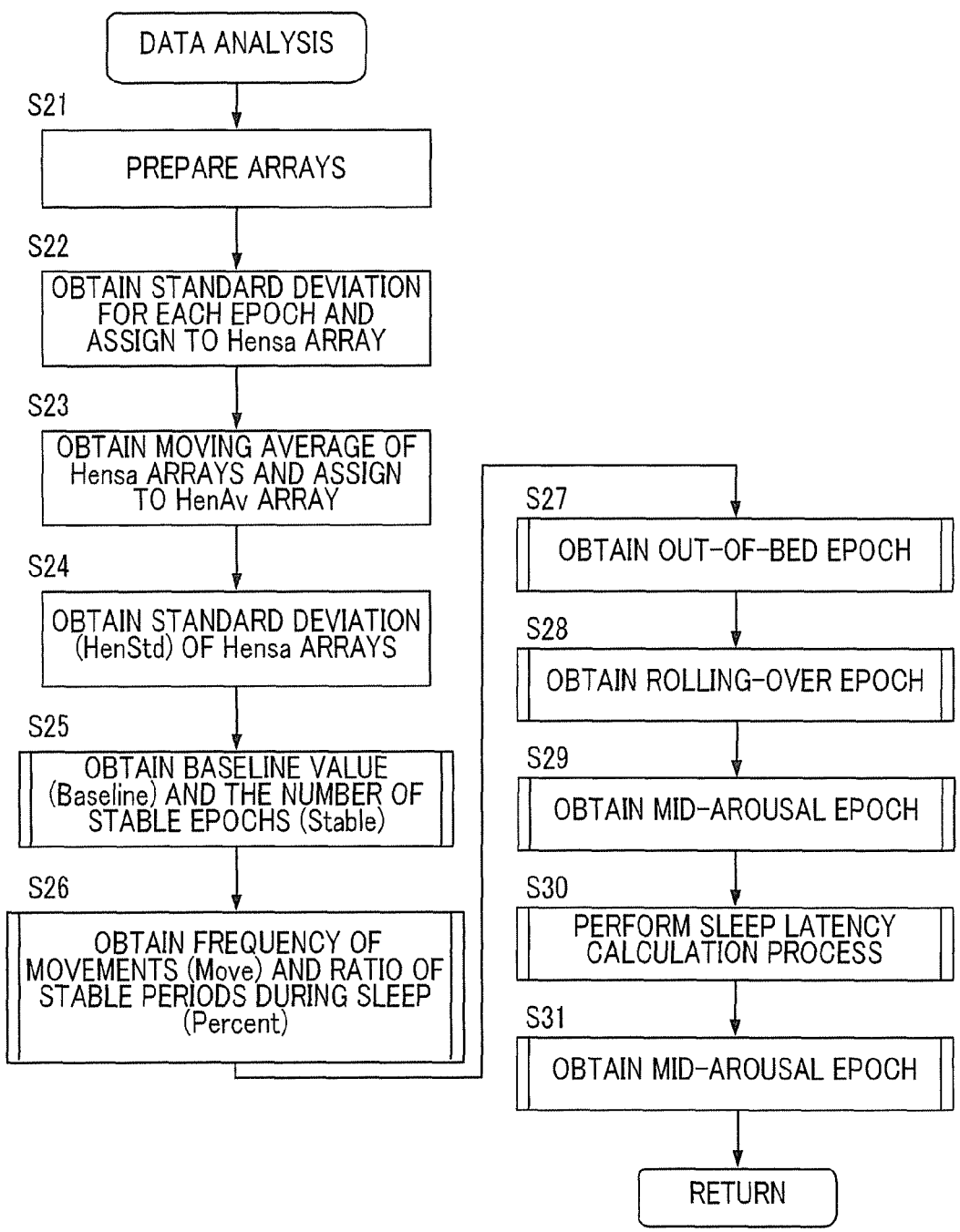
FIG. 5 is a main flowchart of a data analysis process in Step S11 of FIG. 3.

The analyzing unit 30 prepares different types of array variables required for the data analysis according to the present embodiment (Step S21 in FIG. 5). The different types of array variable are, for example, as shown in FIG. 4, Stage [x], Hensa[x], and HenAv[x].

Hensa[x] is a standard deviation of a predetermined number of D[s], D[s+1], ..., and D[s+z] that are selected from the above-described D[0], D[1], ..., D[99], with reference to x, where s is one of 1, 2, ..., 98 and z corresponds to (the predetermined number minus 1). That is, in a case in which AveD=(D[s]+D[s+1]+...+D[s+z])/(z+1) is provided, Hensa [x] is, generally, $$\text{Hensa}[x]=\text{sqr}[(1/(z+1))*SS(D[i]-\text{AveD})^2] \quad (1),$$

in which i=s, s+1, ..., s+z. Furthermore, "sqr" is a square root (hereinafter the same). Furthermore, "SS" means summing i for an expression in ( ). (i.e., this corresponds to the Greek capital letter sigma).

In the present embodiment, it is especially provided that s=10x and z=9. Therefore, as shown in the data table T3 of FIG. 4 as an example, Hensa[0] has a standard deviation of D[0], D[1], ..., D[9], and Hensa[5] has a standard deviation of D[50], D[51], ..., D[59]. Since the total number of body movement data is 100 in the present embodiment, the total of 10 Hensa[x]s: Hensa[0], Hensa[1], ..., and Hensa[9] are defined.

It is to be noted that the calculation process such as described above is the same as a process performed in Step S22 of FIG. 5. Through such a process, each actual value of the Hensa[0], Hensa[1], ..., and Hensa[9] will be written in the data table T3. It is to be noted that the data table T3 corresponds to the address numbers 211 to 220 of the memory storage device 20.

Such Hensa[x] represents, as is understood from the above basis for calculation, or Equation (1), a degree of variation in body movements of a human subject in a certain time period (hereinafter, this will sometimes be referred to as "a unit period"). The unit period in the present embodiment roughly agrees with a time period in which 10 units of body movement data as raw data are obtained by sensor unit 2, as it is clear from the foregoing.

The "unit period" agrees with a period conceptualized by one "group" according to the present invention.

HenAv[x] is a type of moving average value of a predetermined number of Hensa[t], Hensa[t+1], ..., and Hensa[t+y] selected with reference to x from the above-described Hensa [0], Hensa[1], ..., and Hensa[9], in which t is one of 0, 1, 2, ..., and 8, and y is (the predetermined number minus 1). In other words, generally, $$\text{HenAv}[x]=(\text{Hensa}[t],\text{Hensa}[t+1],\ldots,\text{Hensa}[t+y])/(y+1) \quad (2).$$

In the present embodiment, it is specifically provided that t=x-1 and y=2. Therefore, as shown in the data table T4 of FIG. 4 as an example, HenAv[1] has the average value of Hensa[0], Hensa[1], and Hensa[2]. Since the total number of Hensa[x] is 10 in the present embodiment, the total of eight HenAv[x]s: Hensa[1], Hensa[2], ..., and Hensa[8] are defined. In the present embodiment, however, HenAv[0] and HenAv[9] are additionally set, and ten HenAv[x]s are defined in total.

The calculation process such as described above is the same as the process performed in Step S23 of FIG. 5. Through such a process, each actual value of HenAv[0], HenAv[1], ..., and HenAv[9] will be written in the data table T4. The data table T4 corresponds to the address numbers 221 to 230 of the memory storage device 20.

Such HenAv[x], as is understand from the above basis for calculation or Equation (2), represents the average value of degrees of variation in body movements of a human subject in a period conceptualized for Hensa[x−1], Hensa[x], and Hensa[x+1], i.e., three unit periods centering around x.

Thus, HenAv[x] is expressed as:

$$\text{HenAv}[x]=(\text{Hensa}[x-1]+\text{Hensa}[x]+\text{Hensa}[x+1])/3$$

The "moving average value" according to the present invention includes such a case.

Stage[x] represents whether a human subject is in a sleep state or in an aroused state. The x in this case means an "epoch" in the present embodiment. This is the same for x in the above Hensa[x]. As, in the case of Hensa[x], one x represents 10 units of body movement data, for the x in Stage[x], one unit (i.e., "1 epoch") is defined by counting a period in which 10 units of body movement data are acquired as a collective unit. Strictly speaking, Stage[x] serves as a variable that expresses whether the human subject is in a sleep state or in an aroused state for each epoch (i.e., x=1, 2, 3, ... each).

In the data table T2 of FIG. 4, Stage[0] and Stage[9] has a value of "1", meaning that a human subject is in an aroused state in these epochs 0 and 9. On the other hand, Stage[1] has a value of "0", meaning that a human subject is in a sleep state during the epoch 1. The settings of values in each Stage[x] will be performed in the processes in the FIG. 8 (an out-of-bed epoch calculation process), FIG. 9 (a rolling-over epoch calculation process), FIGS. 11 and 12 (a mid-arousal epoch calculation process), FIG. 15 (a sleep latency calculation process), and FIGS. 16 and 17 (a mid-arousal epoch calculation process). Stage[x] will be described again at a later time in describing these processes.

Once Hensa[x] and HenAv[x] are obtained, then analyzing unit 30 obtains a standard deviation HenStd for overall Hensa [x] (Step S24 in FIG. 5). Therefore, $$\text{HenStd}=\text{sqr}[(1/10)*SS(\text{Hensa}[j]-\text{AveHensa})^2] \quad (3),$$

in which j=0, 1, 2, ..., or 9, and AveHensa=(Hensa [0]+...+Hensa[9])/10. Furthermore, "SS" means summing j for an expression in ( ). (i.e., it corresponds to the Greek capital letter sigma).

Figure 6:
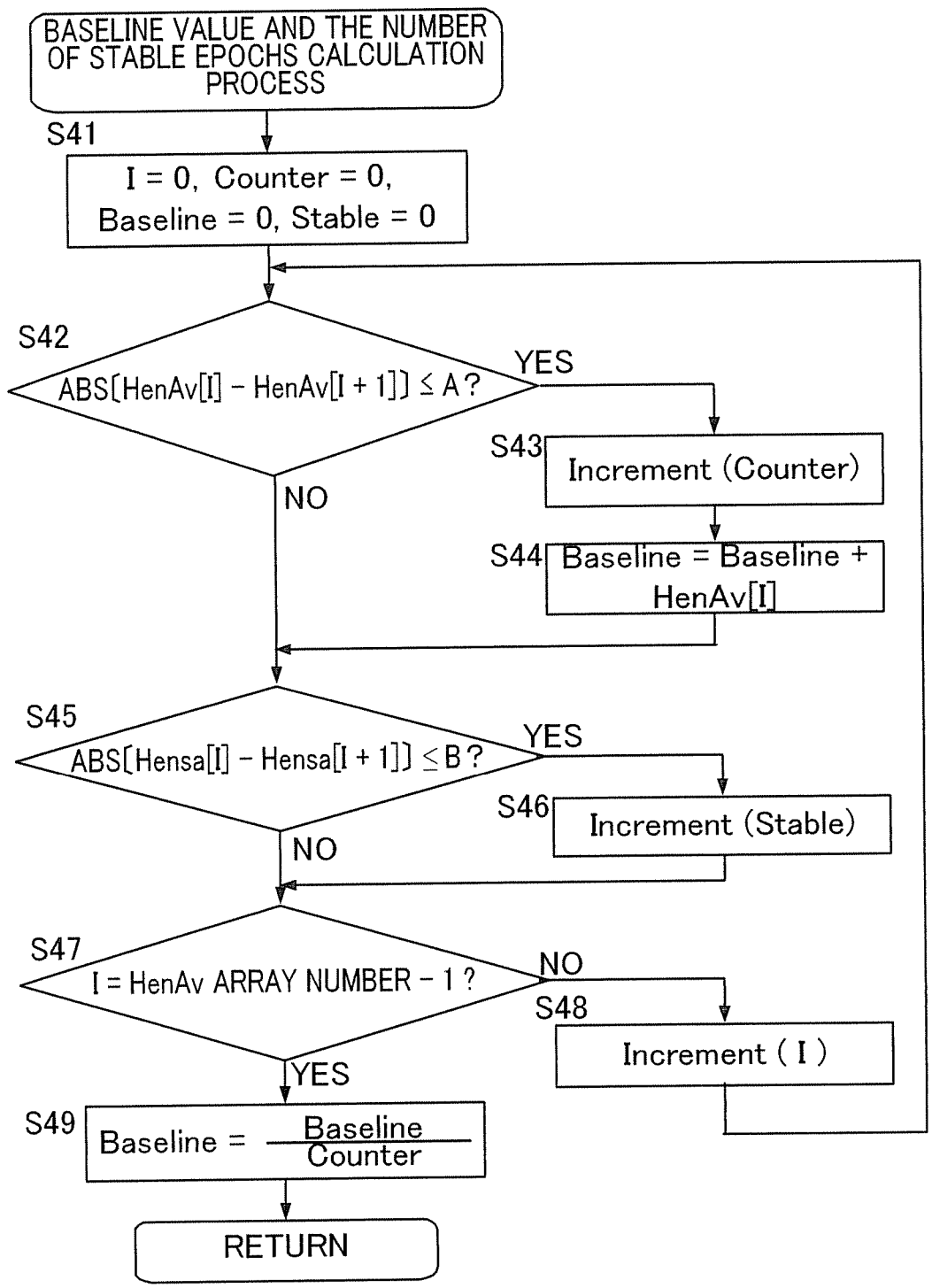
FIG. 6 is a flowchart showing a process of obtaining a baseline value, Baseline, and stable epoch number, Stable.

Analyzing unit 30 obtains a baseline value, Baseline, and the number of stable epochs, Stable (Step S25 in FIG. 5). The details of this process are shown in FIG. 6. The meanings of the baseline value, Baseline, and the number of stable epochs, Stable, will be described later.

In FIG. 6, after the initial settings are performed on variables ("I" and "Counter" in this case), and the number of stable epochs, Stable, and the baseline value, Baseline (Step S41 in FIG. 6), analyzing unit 30 determines "true" or "false" based on the following conditional equation (Step S42 in FIG. 6).

$$ABS[\text{HenAv}[I]-\text{HenAv}[I+1]] \leq A \qquad (4),$$

in which "ABS" means using the absolute value of a value of [ ] (hereinafter the same).

In other words, the conditional expression expresses that the determination is performed as to whether the absolute value of a difference between two consecutive values (or two consecutive unit periods) of HenAv[x] is equal to or less than a predetermined value "A".

In a case in which Equation (4) is true, analyzing unit 30 increments by 1 a value of the variable, "Counter", and increments a value of the variable, "Baseline", by a value corresponding to the HenAv[I] (Step S43 and S44 in FIG. 6).

On the other hand, in a case in which Equation (4) is false, analyzing unit 30 proceeds to determine whether the following conditional expression is true or false (Step S45 in FIG. 6).

$$ABS[\text{Hensa}[I]-\text{Hensa}[I+1]] \leq B \qquad (5)$$

in which B>A.

In a case in which Equation (5) is satisfied, analyzing unit 30 increments a value of the variable, Stable, by 1 (Step S46 in FIG. 6), but in a case in which it is not satisfied, no changes are made to the values of Counter, Baseline, or Stable.

The above process is performed until HenAv[9] is reached (from Step S47: NO to Step S48, and then further to Step S42 in FIG. 6). In a case in which a process up to I+1=9 is finished, $$\text{Baseline}=(\text{Baseline}/\text{Counter}) \qquad (6)$$

is calculated, and the final value of the "baseline value" or "Baseline" is obtained (Step S49 in FIG. 6).

The above process according to FIG. 6 has the following implications.

Since HenAv[x] expresses the average value of degrees of variations in the body movement of a human subject, during three unit periods centered around x, "HenAv[I]−HenAv[I+1]" found in Equation (4) corresponds to the difference between the average value of degrees in variation for the periods (I−1), I, and (I+1) and that for the periods I, (I+1), and (I+2) (Since HenAv is a moving average value, the unit periods partially overlap with each other). The absolute value being equal to or smaller than "A" means that a human subject has maintained a certain degree of stability in a state during the transition from I to (I+1). In this case, as described above, a value of HenAv[I] is added to Baseline (refer to Step S44 in FIG. 6). Repeating the same process for I=1, 2, . . . , the average value of all HenAv[x]s that were added in Step S44 is finally obtained as "Baseline", as shown in Equation (6).

Thus, the baseline value, "Baseline", expresses the average value of selected HenAv[x] that corresponds to a case in which a certain degree of stability in a state was maintained.

In contrast, when the absolute value shown in Equation (5) is equal to or less than "B(>A)" means that a human subject did not perform a relatively large body movement, such as a rolling over, in the transition from the same period I to (I+1) (however, the value to be compared to B is Hensa[x]). In this case, the value of the number of stable epochs, Stable, is increased during a period of the transition, so that the fact that no roll-overs occurred is recorded. If a human subject supposedly did not roll over at all during the measurement period, the process in Step S46 in FIG. 6 is inevitably performed, and the value of Stable will be (I−1).

Thus, the number of stable epochs, Stable, indicates the number of periods (this period can be counted based on a unit period as a standard or as a unit) in which there was no relatively large body movement of a human subject.

Once the baseline value, Baseline, and the number of stable epochs, Stable, are obtained as described above, analyzing unit 30 then obtains an index, Move, showing the frequency of movements and the ratio of stable periods during sleep, Percent, (Step S26 in FIG. 5). The details of this process are shown in FIG. 7.

Figure 7:
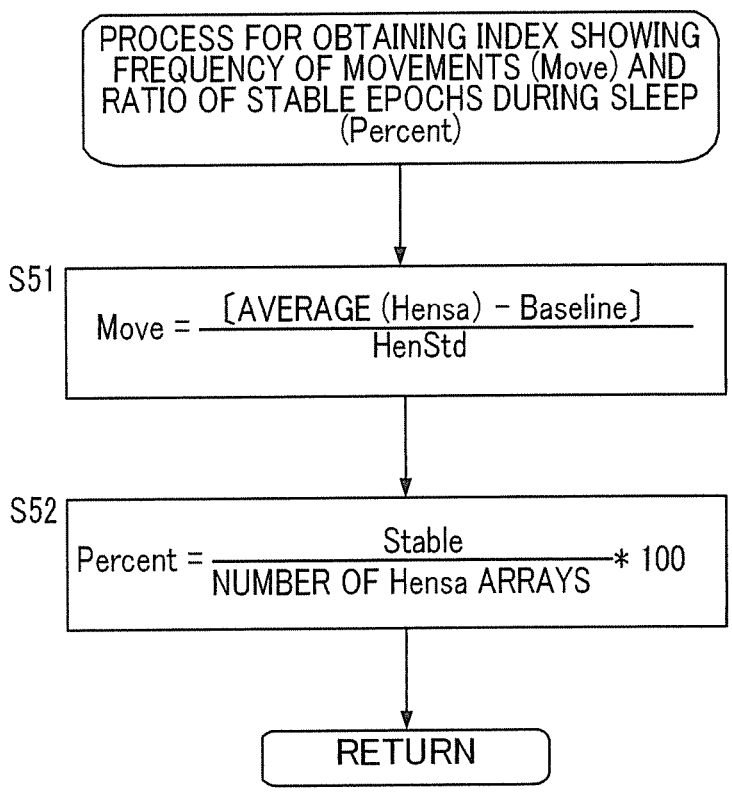
FIG. 7 is a flowchart showing a process of obtaining an index, Move, showing the frequency of movements and the ratio of Stable during sleep.

As shown in FIG. 7, the Move is obtained as a value obtained by subtracting the baseline value, Baseline, obtained above from the average value of the Hensa[x] (the same as "AveHensa" appearing in the above Equation (3)) and dividing the subtracted result by HenStd (Step S51 in FIG. 7). As this value of the Move is greater, the movement of a human subject is more frequent.

Furthermore, the Percent is 100 times of the number of stable epochs, Stable, divided by the number of arrays of the Hensa[x], i.e., 10 (the total number of "unit periods") in the present embodiment (Step S52 in FIG. 7).

Subsequently, analyzing unit 30 obtains an out-of-bed epoch (Step S27 in FIG. 5). The details of this process are shown in FIG. 8.

Figure 8:
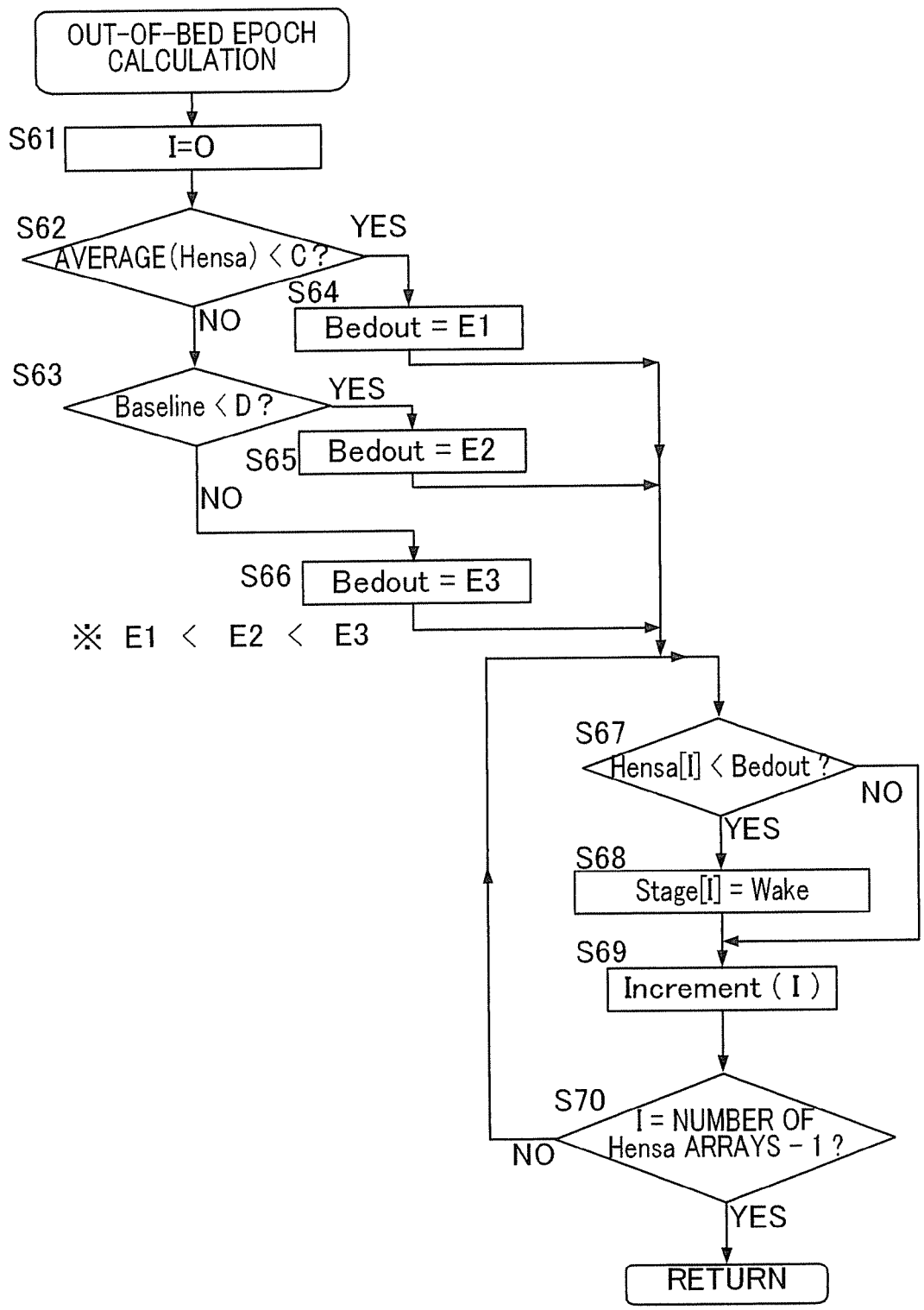
FIG. 8 is a flowchart showing an out-of-bed epoch calculation process.

In FIG. 8, after the initial setting is performed on a variable (in this case, "I") (Step S61 in FIG. 8), analyzing unit 30 determines whether the average value of the Hensa[x] (the same as "AveHensa" in the above Equation (3)) falls below a predetermined value C (Step S62 in FIG. 8). In a case in which it is determined that it falls below the predetermined value C (Step S62 in FIG. 8: YES), a predetermined value E1 is assigned to a variable, Bedout (Step S64 in FIG. 8).

On the other hand, in a case in which it does not fall below the predetermined value C (Step S62 in FIG. 8: NO), it is then determined whether the baseline value, Baseline, falls below a predetermined value D (Step S63 in FIG. 8). In a case in which the baseline value, Baseline, falls below the predetermined value D (Step S63: YES in FIG. 8), a predetermined value E2 is assigned to the variable, Bedout (Step S65 in FIG. 8). On the other hand, in a case in which it does not, a predetermined value E3 is assigned to the variable, Bedout (Step S66 in FIG. 8).

The E1, E2, and E3 satisfy E1<E2<E3.

Analyzing unit 30 then determines whether a value of Hensa[I] falls below the variable, Bedout, that has a value, depending on a result of the above determination, E1, E2, or E3 (Step S67 in FIG. 8). In a case in which it falls below the predetermined number, "Wake" is assigned to Stage[x] (Step S68 in FIG. 8). On the other hand, if this is not the case, no changes are made to a value of Stage[x] (refer to Step S67: NO in FIG. 8).

In the present embodiment, this process is performed until Hensa[9] is reached (refer to Steps S69 and S70 in FIG. 8).

The above-described "Wake" corresponds to a value "1" shown in the data table T2 of FIG. 4. Therefore, a value "0" shown in the data table T2 of FIG. 4 means a case that is not "Wake". This will be hereinafter the same.

This process according to FIG. 8 has the following implications.

In this process, a value of Stage[x] described with reference to FIG. 4 is determined for each epoch. In this case, in FIG. 8, as it is understood from the value of "Bedout" in Step S67 having a different value: E1, E2, or E3, the basis is changed for determination as to whether a human subject is in bed or out of bed. Each basal value, Bedout, specifically, E1, E2, or E3, is an extremely small value, and this value serves to detect a situation (or an epoch) in which sensor unit 2 is not sensing a body movement of a human subject. This is a reason why it is set as Stage[I]="Wake" in a case in which Hensa[I]<Bedout is true.

Furthermore, as it is understood from conditions in which E1<E2<E3 is true, and that E1 corresponds to a case in which AveHensa<C is true, E2 corresponds to a case in which the baseline value, Baseline<D is true, and E3 corresponds to other cases, E1 to E3 are defined depending on a degree of stability of a human subject during sleep. Since a case in which AveHensa falls below C means a case in which the variation in body movements of a human subject throughout all the periods is relatively small, a smaller basal value E1 should be preferably used to determine whether an "out-of-bed" state has taken place. On the other hand, in a case in which Baseline falls below D (and AveHensa≥C), Baseline is the average value of HenAv[x]s, the HenAv[x]s having been selected assuming, as described above, that Baseline corresponds to a case in which a certain degree of stable state is maintained. Therefore, it can be inferred that this human subject is relatively quiet, at least in a stable period, and thus, a basal value E2 that is greater than E1 is preferably used.

The other cases are those in which the above two cases are not true, and therefore, a basal value E3 that is greater than the E2 is preferable.

In summary, in the present embodiment, the determination as to whether an "out-of-bed" state has taken place is based on differences in general characteristics of body movements of a human subject during sleep.

Once an out-of-bed epoch is determined in a way described above, then analyzing unit 30 obtains a rolling over epoch (Step S28 in FIG. 5). The details of this process are shown in FIG. 9.

Figure 9:
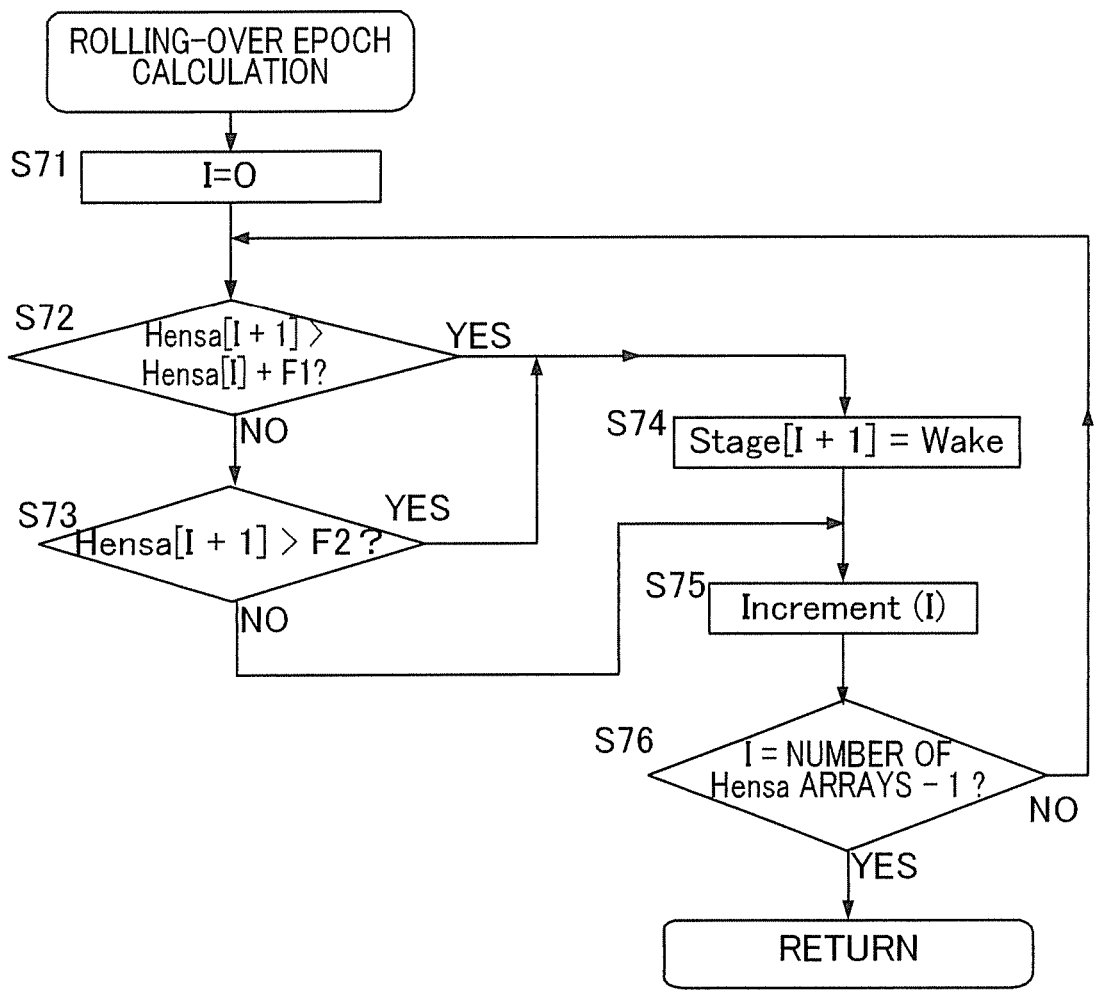
FIG. 9 is a flowchart showing a rolling over epoch calculation process.

In FIG. 9, after an initial settings is performed on a variable ("I" in this case) (Step S71 in FIG. 9), analyzing unit 30 determines whether the following conditional expression is true or false (Step S72 in FIG. 9).

$$\text{Hensa}[I+1] > \text{Hensa}[I] + F1 \qquad (7)$$

In a case in which this is determined to be false, another determination is made as to whether the following conditional expression is true or false (Step S73 in FIG. 9).

$$\text{Hensa}[I+1] > F2 \qquad (8)$$

In a case in which either Equation (7) or (8) is determined to be true (Step S72: YES, or S73: YES, in FIG. 9), "Wake" is assigned to Stage[I+1] (Step S74 in FIG. 9). On the other hand, in a case in which both equations are determined to be false (Step S73: NO in FIG. 9), no changes will be made to Stage[I+1] (Step S75 in FIG. 9).

In the present embodiment, such a process is repeated until Hensa[9] is reached (refer to Step S76 in FIG. 9).

The process according to FIG. 9 has the following implications.

That is, in this process, in a case in which the standard deviation Hensa[I+1] of the body movements of a human subject in a given period (I+1) increases "in comparison" with the period I, or in a case in which the standard deviation Hensa[I+1] itself is "absolutely" large, this period (I+1) is determined as an epoch in which a "rolling over" has taken place. This event of a "rolling over" can be regarded to be the same as, at this point in time, the human subject being "awake" or "arisen". This is because brain waves that are observed when a "rolling over" is taking place can be regarded in the same way as those when the human subject is in the aroused state.

Thus, in this process, in a case in which a rolling over takes place even though it was not determined as being "Wake" in the above out-of-bed epoch calculation process, it is determined that this epoch is also "Wake".

After the processes according to FIGS. 8 and 9 are performed, each Stage[x] will have a value as shown as an example in FIG. 10. The exemplary values in this FIG. 10 show that, as a result of the process according to FIG. 8, an "out-of-bed" takes place in Stage[0], Stage[2], and Stage[9], and that after the process according to FIG. 9, a "rolling over" takes place in Stage[7]. (The values of Stage[0], Stage[2], and Stage[9] are retained as they were before the processes according to FIGS. 8 and 9 are performed, as indicated by the arrows shown in the figure.)

Subsequently, analyzing unit 30 obtains a mid-arousal epoch (Step S29 in FIG. 5). The details of this process are shown in FIGS. 11 and 12.

Figure 11:
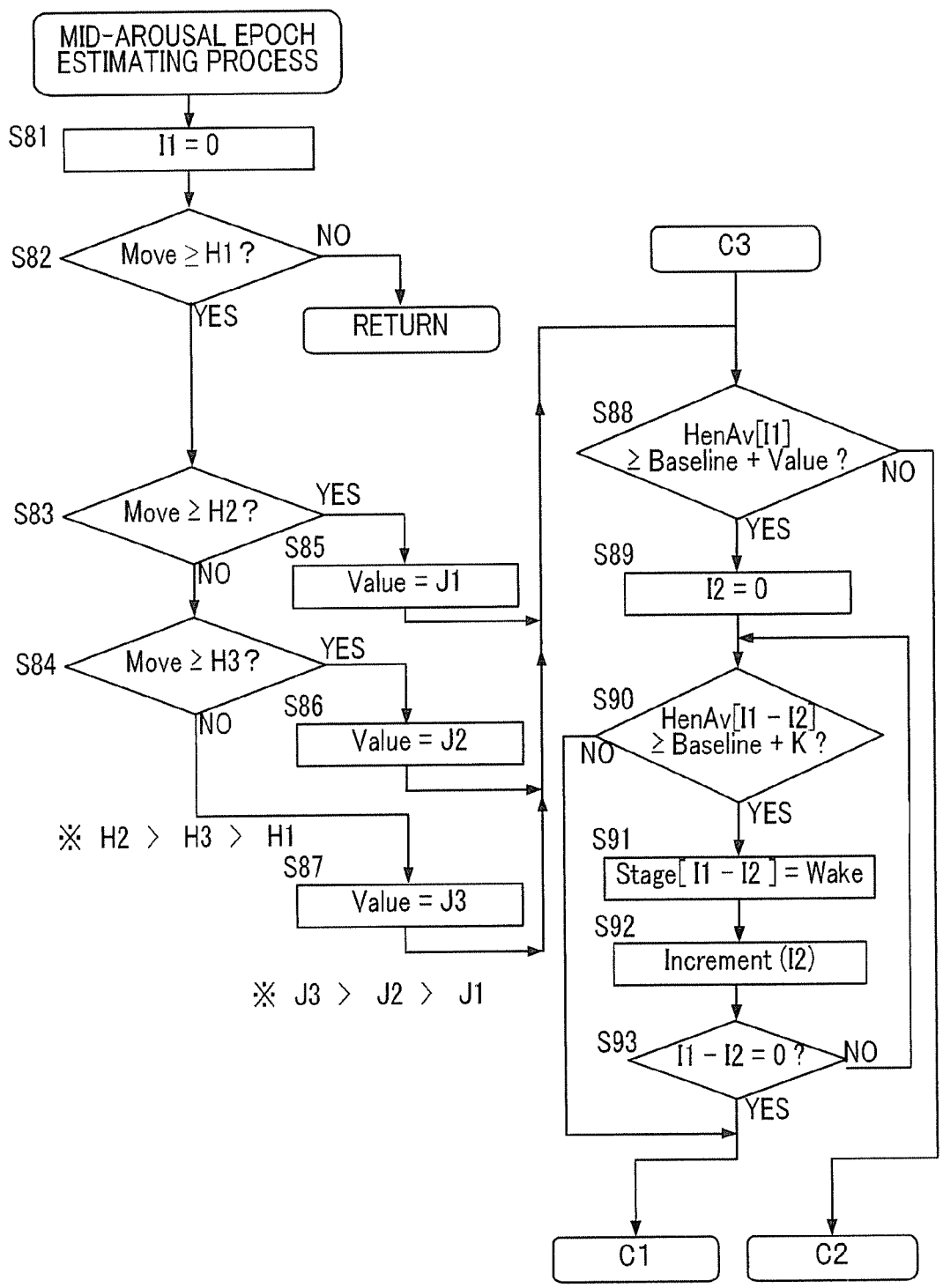
FIG. 11 is a first half of a flowchart showing a mid-arousal epoch calculation process.
Figure 12:
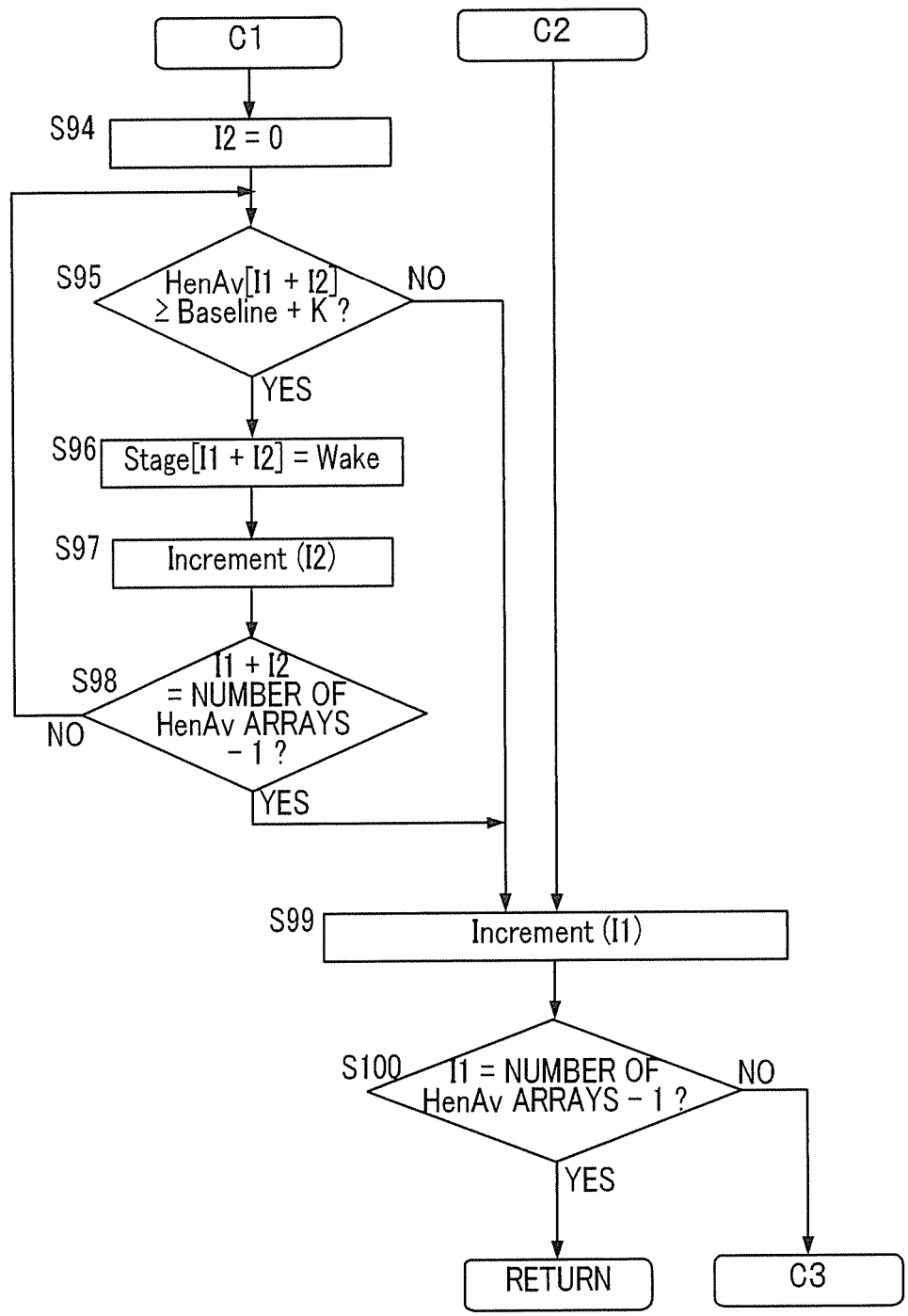
FIG. 12 is a second half of the flowchart showing the mid-arousal epoch calculation process.

In FIG. 1, after an initial setting is performed on another variable (I1 in this case) (Step S81 in FIG. 11), analyzing unit 30 determines whether the above obtained index, Move, indicating the frequency of movements (refer to FIG. 5) is equal to or greater than H1 (Step S82 in FIG. 11). In a case in which it is determined to be false, the routine returns to the main flowchart according to the data analysis process of FIG. 5. This is because, at this point in time, it is already finally decided that "the human subject was not awake during sleep", i.e., "there was no mid-arousal".

On the other hand, in a case in which a result of the determination of Step S82 is true, analyzing unit 30 then determines whether Move is equal to or greater than H2 (Step S83 in FIG. 11), and in a case in which this is false, it is further determined whether Move is equal to or greater than H3 (Step S84 in FIG. 11). In a case in which the result of the determination of Step S83 is true, J1 is assigned to a variable, Value, (Step S85 in FIG. 11). In a case in which a result of the determination of Step S84 is true, J2 is assigned to Value (Step S86 in FIG. 11). Furthermore, in a case in which both results of the determinations of Steps S83 and S84 are false, J3 is assigned to Value (Step S87 in FIG. 11).

The above H1, H2 and H3 satisfy H2>H3>H1. Furthermore, the above J1, J2 and J3 satisfy J3>J2>J1.

Subsequently, analyzing unit 30 determines whether the following conditional expression is true or false (Step S88 in FIG. 11).

$$\text{HenAv}[I1] \geq \text{Baseline} + \text{Value} \qquad (9)$$

In a case in which this is determined to be true, analyzing unit 30 determines whether HenAv[I1−I2]≥Baseline+K is true or not (Step S90 in FIG. 11) after initializing a variable (I2 in this case) (Step S89 in FIG. 11). In a case in which this is determined to be true, "Wake" is assigned to Stage [I1−I2] (Step S91 in FIG. 11). Then, in Step S92, the value of I2 is incremented by 1.

This process using I2 is performed repeatedly until the value of I2 reaches the value of I1 as of a point in time at which this process was started (refer to Steps S92 and S93 in FIG. 11).

On the other hand, in the above Step S90, in a case in which HenAv[I1−I2]≥Baseline+K is determined to be false, analyzing unit 30 determines whether HenAv[I1+I2]≥Baseline+K is true (Step S95 in FIG. 12) after initializing the variable (I2 in this case), (from Connection symbol "C1" of FIGS. 11 and 12 to Step S94 in FIG. 12). In a case in which a result of the determination of Step S95 is true, "Wake" is assigned to Stage[I1+I2] (Step S96 in FIG. 12).

This process using I2 is performed repeatedly until a value obtained by adding I2 and I1 as of a point in time at which this process was started agrees with the total number of HenAv arrays (refer to Steps S97 and S98 in FIG. 12).

In the processes from Step S89 in FIG. 11 to Step S98 in FIG. 12, a value of Stage[x] could be changed; however, in a case in which, in the above Step S88 in FIG. 11, HenAv[I1]≥Baseline+Value is determined to be false, analyzing unit 30 does not change a value of Stage[x] (refer to the flow from Step S88: NO in FIG. 11, to Connection symbol "C2", and to Step S99 in FIG. 12).

In each of the above processes, those from Steps S88 to S98 are performed until HenAv[9] is reached in the present embodiment (refer to Steps S99 and S100 in FIG. 12 and Connection symbol "C3" in FIGS. 12 and 11).

This process according to FIGS. 11 and 12 has the following implications.

That is, the first half of this process, i.e., the process from Steps 82 to S87 in FIG. 11 in which J1 to J3 are set based on H1 to H3 means setting a basal value depending on the frequency of movements of a human subject. In other words, in a case in which the movement of a human subject is extremely active (i.e., Move≥H2 (>H3>H1)), the basal value is set to the minimum J1, and otherwise (i.e., H2>Move≥H3(>H1)), the basal value is set to J2 of a medium degree, and in a case in which the movement is minimal (i.e., H3>Move≥H1), the basal value is set to the maximum J3.

Therefore, figuratively speaking, J1, J2, and J3 serve as bias values as is understood from Equation (9). Specifically, as described above, although the process with respect to I1 is completed if Equation (9) is false, as the movement of a human subject changes from being extremely active, to being moderate, and then to being minimal, the basal value gradually becomes greater, and the basal value indicating whether Stage[x] could be changed.

It should be noted that, in a case in which the movement of a human subject is extremely minimal (i.e., Move<H1), no process of setting the basal value or the subsequent processes is performed.

The above examples are shown in a table in FIG. 13.

After such a basal value, Value, is set, the second half of the process, i.e., the process from Step S88 in FIG. 11 to Step S100 in FIG. 12, will be performed to obtain a mid-arousal epoch. This process can be considered as having two types of processes.

The first type of process is a process from Steps S89 to S93 in FIG. 11. In this process, it is determined whether there was any event of mid-arousal at a point in time that is earlier in time with reference to the period I1 (determination at "a point in time that is earlier in time" means that, in this first type of process, the determination is performed with reference to I1, i.e., as I1−0, I1−1, I1−2, . . . ). Furthermore, the basis for the determination is "Baseline+K" (refer to Step S90 in FIG. 11). Then, in a case in which HenAv[I1−I2] is equal to or greater than the value of "Baseline+K", it is determined that "there is a mid-arousal", and "Wake" is assigned to Stage[x].

On the other hand, the second type of process is a process from Steps S94 to S98 in FIG. 12. In this process, it is determined whether there was any event of mid-arousal at a point in time that is later in time with reference to the period I1 (determination at "a point in time that is later in time" means that, in this second type of process, the determination is performed with reference to I1, i.e., as I1+0, I1+1, I1+2, . . . ). The basis for determination used is the same as that used in the first type of process (refer to Step S95 in FIG. 12).

Figure 14:
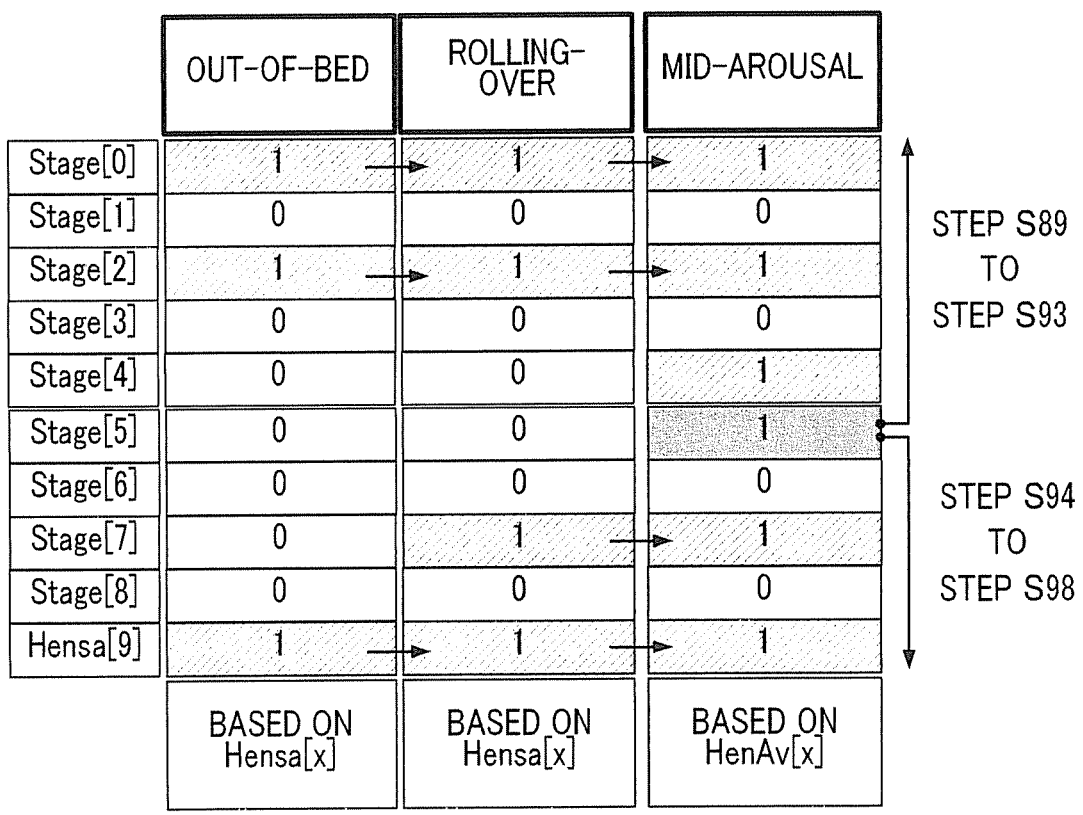
FIG. 14 is an explanatory diagram showing specific values of Stage[x] that have been set as a result of the process of FIGS. 11 and 12.

The above process is visually and ideally shown in FIG. 14. That is, in this FIG. 14, given that the above I1 is 5, the search for a mid-arousal epoch is performed backward and forward with reference to this point, as shown by upward and downward arrows in the figure. FIG. 14 also shows an example in which, in addition to Stage[5], Stage[4] is determined as a mid-arousal epoch. It is to be noted that the left portion of FIG. 14 is the same as that in FIG. 10, and the implications of right-pointing arrows in the figure are the same as that which has been described with reference to FIG. 10.

Accordingly, in the process according to FIGS. 11 and 12, a sleep state of a human subject in epoch I1 is evaluated first on the basis of an index, Move, and the baseline value, Baseline (refer to Step S88 in FIG. 12), and then based on this evaluation, it is posteriori and cyclopaedically determined whether there was a mid-arousal or not (refer to the above description on the first-type and the second-type processes).

Mid-arousal epochs are obtained in the manner described above, and analyzing unit 30 then performs a sleep latency calculation process (Step S30 in FIG. 5). The details of this process are shown in FIG. 15.

Figure 15:
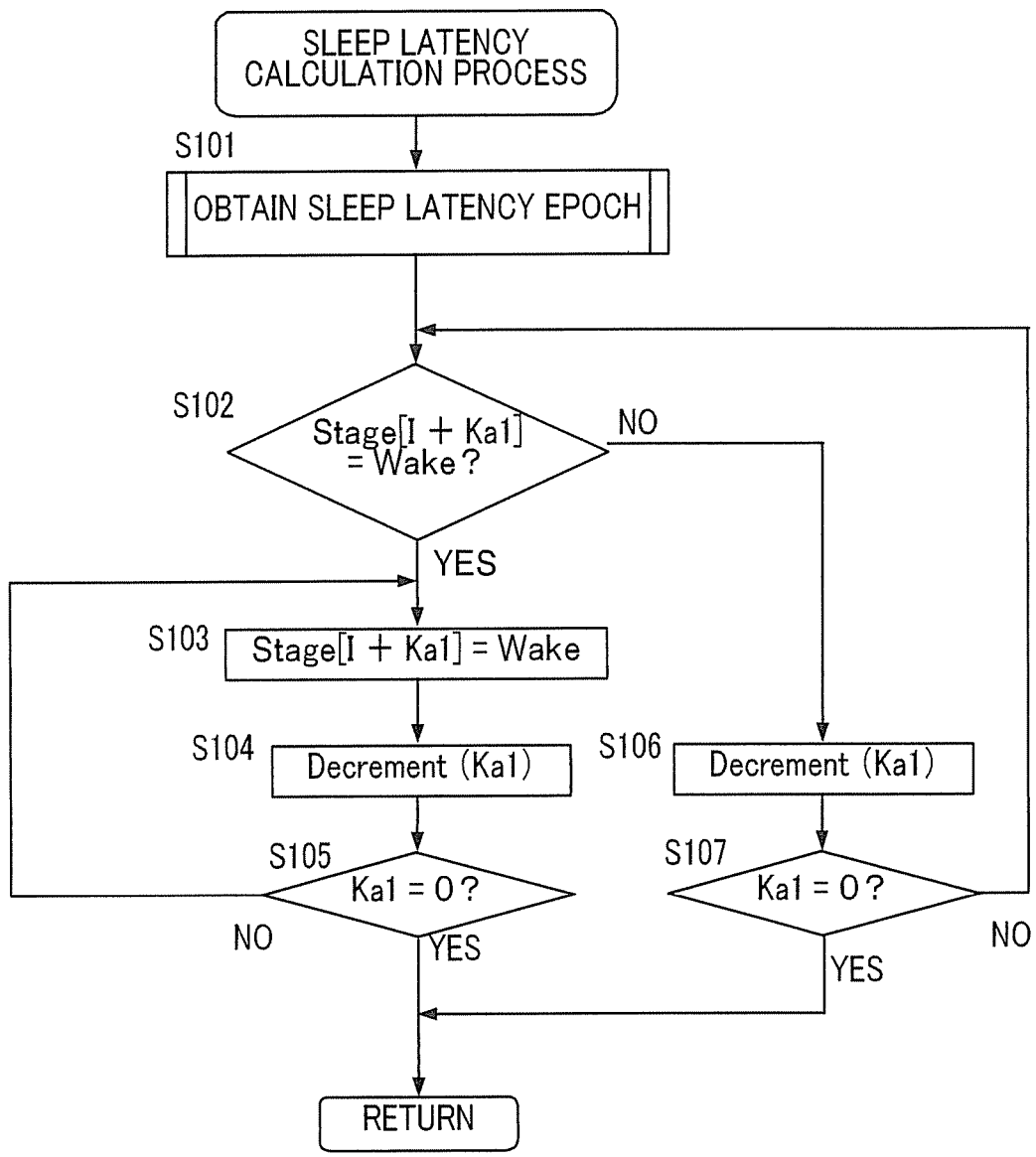
FIG. 15 is flowchart showing a sleep latency calculation process.

In FIG. 15, analyzing unit 30 obtains a sleep latency epoch (Step S101 in FIG. 15).

Figure 18:
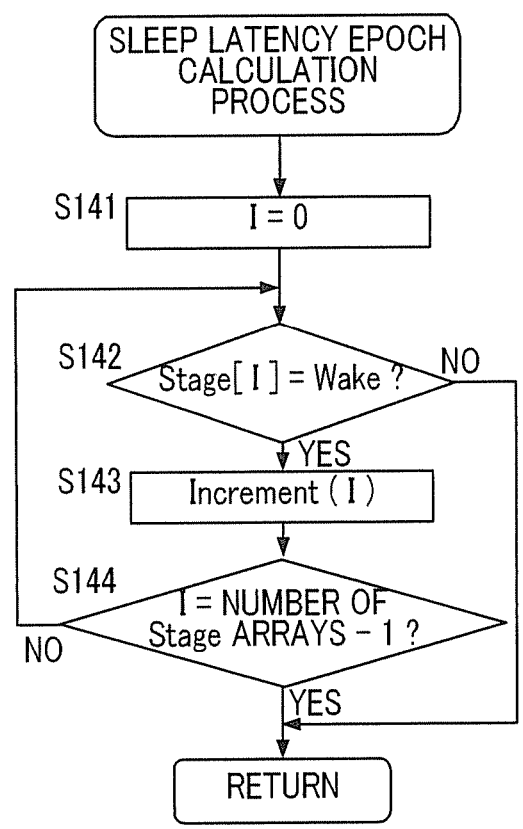
FIG. 18 is a flowchart showing a sleep latency epoch calculation process.

The details of this step are shown in FIG. 18. In this sleep latency epoch calculation process, after initializing a variable (I in this case), (Step S141 in FIG. 18), analyzing unit 30 determines whether Stage[I] corresponds to "Wake" (Step S142 in FIG. 18). If this is negative, the routine returns to the main process of FIG. 15 (from Step S142 in FIG. 18: NO, to Step S102 in FIG. 15). On the other hand, if the determination is affirmative, I is increased by 1, to repeat the subsequent process (refer to Step S142:YES, Steps S143 and S144 in FIG. 18).

Thus, in this sleep latency epoch calculation process, Stage [x] that does not have "Wake" is searched for. Therefore, when the process of FIG. 18 is completed, a value of "I" (hereinafter, this will sometimes be referred to as "I as of sleep latency") in a case in which Stage[I] does not have a value, "Wake", or a value of "I" in a case in which Stage[I] no longer has a value, "Wake", as I is incremented will be returned to the main process (the process of FIG. 15).

Subsequently, analyzing unit 30 determines whether Stage [I+Ka1] has a value, "Wake" (Step S102 in FIG. 15). If this is affirmative, a value, "Wake", is reassigned to Stage[I+Ka1] (Step S103 in FIG. 15), and then Ka1 is decremented by 1 (Step S104 in FIG. 15). Such assignment processes and subtraction processes are performed until Ka1 reaches 0 (refer to the flow from Steps S105 to S103 in FIG. 15). As a result, all Stage[x0]s having array numbers, x0=I+1, I+2, . . . , I+Ka1, will have values, "Wake"s.

On the other hand, in the above Step S102, if Stage[I+Ka1] is not Wake, Ka1 will be simply incremented by 1 (Step S106 in FIG. 15). Such a process will be repeated until Ka1 reaches 0 or until Stage[I+Ka1] that agrees with Wake is hit (refer to Step S107 in FIG. 15). If Stage[I+Ka1] that agrees with Wake is found, the above-described process will be executed.

The process according to FIG. 15 has the following implications.

That is, if there is any epoch (I+Ka1) satisfying Stage[I+Ka1]=Wake at a point in time that is away from I as of sleep latency by an arbitrary set Ka1, this point in time cannot be determined as an epoch in which a human subject enters a sleep state in a true sense. This is based on an empirical rule or a logical rule that a "rolling over is usually unlikely to take place immediately after "sleep latency" (i.e., an epoch at such a point in time usually will not be "Wake"). Therefore, in such a case, Stage[I+1], Stage[I+2], . . . , and Stage[I+Ka1] will be redetermined as being aroused states.

Thus, according to the process of FIG. 15, for the accurate determination of a period in which a human subject was in a sleep state in a true sense, a case in which Stage[x] that does not have Wake is searched for as an error, and Stage[x] that has been thus retrieved is reset as Wake.

In a case in which the sleep latency calculation process is completed in such a way as above, analyzing unit 30 obtains a mid-arousal epoch (Step S31 in FIG. 5). The details of this process are shown in FIGS. 16 and 17.

Figure 16:
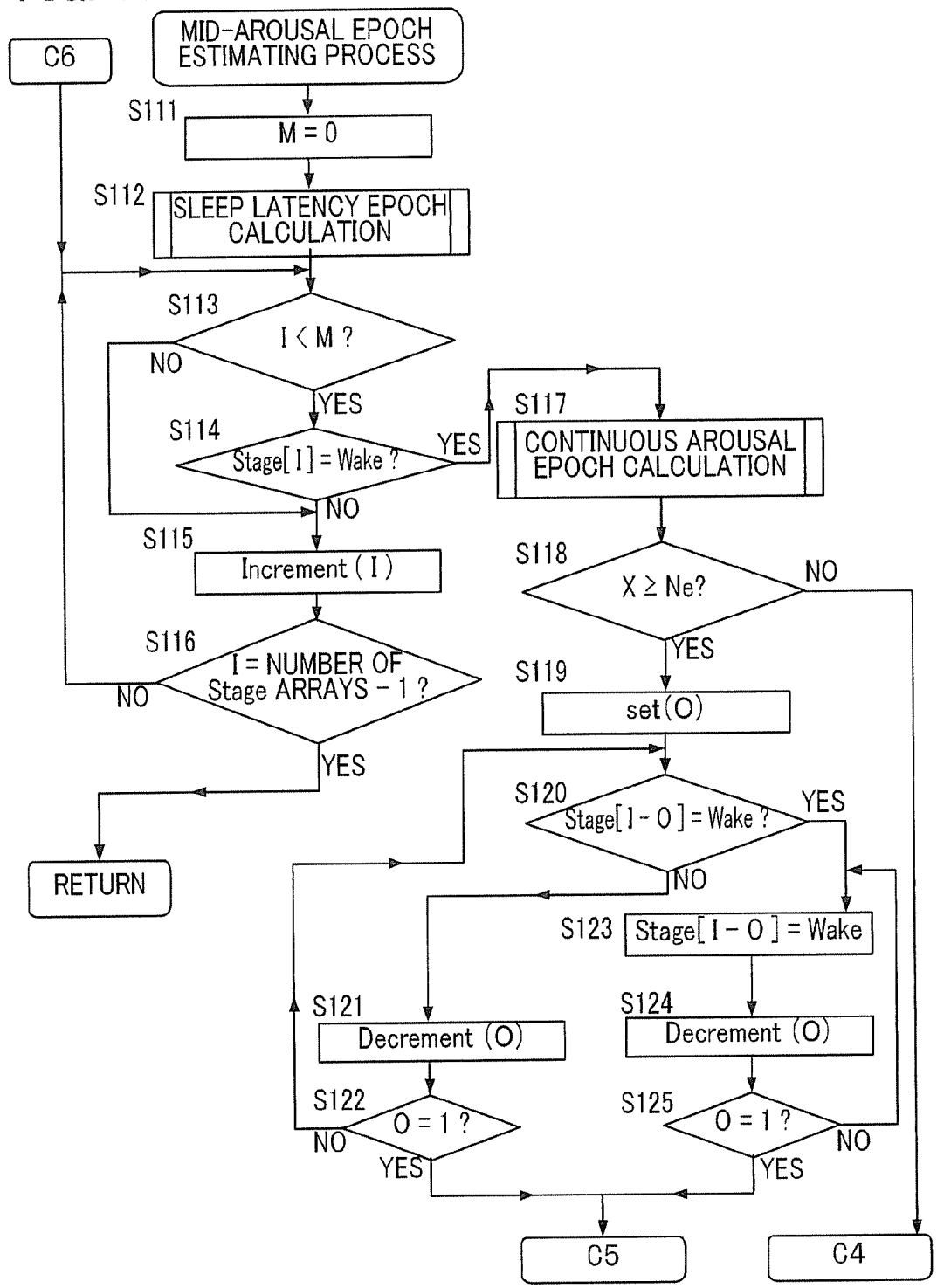
FIG. 16 is a first half of a flowchart showing a mid-arousal epoch calculation process which is a supplemental process of FIGS. 11 and 12.
Figure 17:
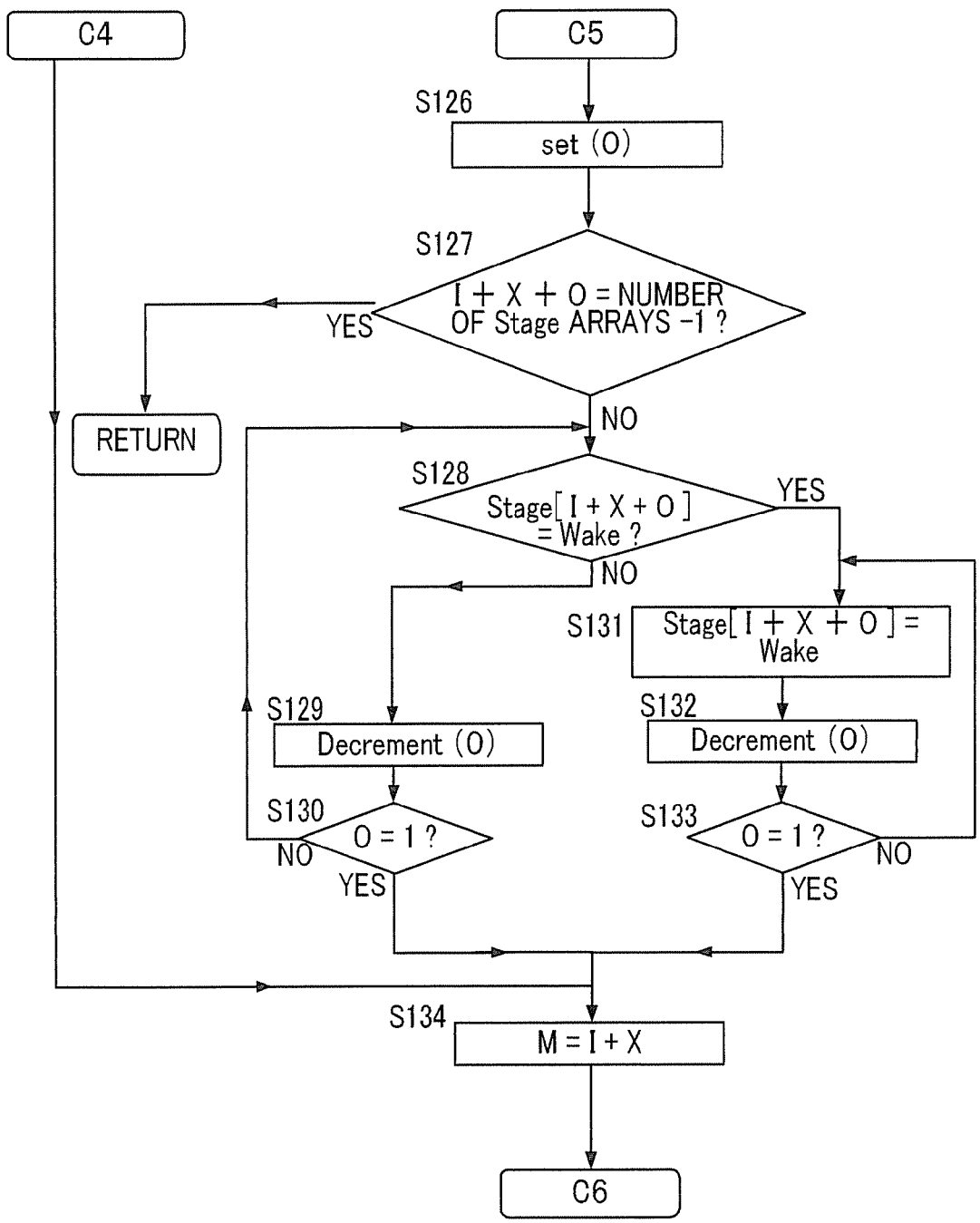
FIG. 17 is a second half of the flowchart showing the mid-arousal epoch calculation process which is a supplemental process of FIGS. 11 and 12.

In FIG. 16, after initializing a variable (M in this case) (Step S111 in FIG. 16), analyzing unit 30 obtains a sleep latency epoch (Step S112 in FIG. 16). In this step, the above-described process shown in FIG. 18 is performed. Therefore, when the process of FIG. 18 is finished, I as of sleep latency will be acquired.

Analyzing unit 30 subsequently determines whether I as of sleep latency falls below M (Step S113 in FIG. 16). In a case in which it is determined that it falls below M, then it is determined whether Stage[I] agrees with "Wake" (Step S114 in FIG. 16). In a case in which Stage[I] agrees with "Wake", analyzing unit 30 proceeds to a continuous arousal epoch calculation process (from Step S114: YES, to Step S117 in FIG. 16). On the other hand, in a case in which, in Step S113, I≥M is satisfied, the determination according to Step S114 will not be performed (Step S113: NO, to Step S115 in FIG. 16).

Such a process will be repeatedly performed on each I which has been incremented by 1 with reference to I as of sleep latency (refer to Steps S115 and S116 in FIG. 16).

The number of repeating process is limited to the total number of Stage[x]s (the total number of epochs) (refer to Step S116 in FIG. 16). If this limit is reached, the routine returns to the data analysis process according to the main flowchart of FIG. 5.

Figure 19:
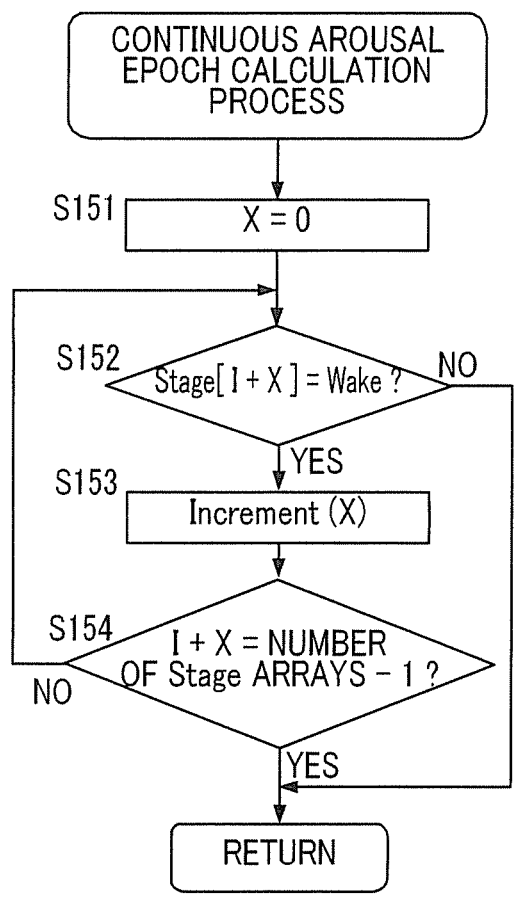
FIG. 19 is a flowchart showing an arousal epoch calculation process.

The details of the continuous arousal epoch calculation process are shown in FIG. 19. In the continuous arousal epoch calculation process, after an initial setting is performed on a variable (X in this case) (Step S151 in FIG. 19), analyzing unit 30 determines whether Stage[I+X] corresponds to "Wake" (Step S152 in FIG. 19). At this point in time, I should satisfy Stage[I]=Wake as long as the affirmative determination was given to the above Step S114 (in other words, at this point in time, I is no longer "I as of sleep latency").

If in Step S152 Stage[I+X]=Wake is negative, the routine returns to the main process (from Step S152: NO in FIG. 19, to Step S116 in FIG. 16). On the other hand, if it is affirmative, X is incremented by 1, and the routine repeats the subsequent process (refer to Step S152: YES, and Steps S153 and S154 in FIG. 19).

Thus, in this continuous arousal epoch calculation process, it is determined to what extent "Wake" is maintained in Stage [x], in which x is equal to or greater than I at a point in time at which a sleep stage advances from "I as of sleep latency" to an aroused state. This I will hereinafter be sometimes referred to as "I as of the start of an aroused state". Therefore, when the process in FIG. 19 is finished, a value of "X" in a case in which Stage[I+X] does not have a value, "Wake", will be returned to the main process (the process in FIG. 16), or a value of "X" in a case in which Stage[I+X] no longer has a value, "Wake", as X is incremented will be returned to the main process (hereinafter, such X will be sometimes referred to as "X of the continuous arousal").

Analyzing unit 30 then determines whether X of the continuous arousal is equal to or greater than Ne (Step S118 in FIG. 16). If this is affirmative, the following process will be performed.

After an appropriate value is set to a variable O (Step S119 in FIG. 16), analyzing unit 30 determines whether Stage[I−O] has "Wake" (Step S120 in FIG. 16). In a case in which this is affirmative, "Wake" is reassigned to Stage[I−O] (Step S123 in FIG. 16), O is decremented by 1 (Step S124 in FIG. 16). Such a process is repeated until O reaches 1 (refer to the flow from Steps S125 to S123 in FIG. 16). As a result, all Stage[x1]s having an array number x1 that is back in time by O since the initial I as of the start of arousal will have a value "Wake".

On the other hand, in the above Step S123, if Stage[I−O] is not Wake, O will be simply decremented by 1 (Step S121 in FIG. 16). Such a process will be repeated until O reaches 1 or Stage[I−O] that agrees with Wake is found (refer to the flow from Steps S122 to S120 in FIG. 16). In a case in which Stage[I−O] that agrees with Wake is found, the above described process will be executed.

When the foregoing process is completed, analyzing unit 30 then proceeds to a process of FIG. 17 (refer to Connection symbol "C5" in FIGS. 16 and 17), an arbitrary value will be again set to variable O (Step S126 in FIG. 17).

Analyzing unit 30, in a case in which it is determined that the sum of I as of the start of arousal, X as of the continuous arousal, and the arbitrarily set O agrees with the total number of epochs, the routine returns to the main flowchart of the data analysis process of FIG. 5 (Step S127: YES in FIG. 17). Otherwise, the following process will be performed (Step S127: NO in FIG. 17).

That is, analyzing unit 30 determines whether Stage[I+X+O] has "Wake" (Step S128 in FIG. 17). In a case in which this is affirmative, "Wake" is reassigned to Stage[I+X+O] (Step S131 in FIG. 17), and then O is decremented by 1 (Step S132 in FIG. 17). Such a process is repeated until O reaches 1 (refer to Step S133 to Step S131 in FIG. 17). As a result, all Stage [x2]s having array numbers x2 up to the point in time that is later in time by O from a value obtained by adding X as of the continuous arousal to the initial I as of the start of arousal will have values "Wake"s.

On the other hand, in the above Step S128, if Stage[I+X+O] is not Wake, O will simply be decremented by 1 (Step S129 in FIG. 17). Such a process is repeated until O reaches 1 or until Stage[I+X+O] that agrees with Wake is found (refer to the flow from Steps S130 to S128 in FIG. 17). In a case in which Stage[I+X+O] that agrees with Wake is found, the above described process will be executed.

In a case in which either the above Step S130 or S133 is determined to be YES (i.e., a case in which O=1 is satisfied), analyzing unit 30 assigns I+X to M (Step S134 in FIG. 17) and then returns to the process of FIG. 16 (refer to Connection symbol "C6" in FIGS. 17 and 16).

On the other hand, in a case in which, in the above Step S118 in FIG. 16, X≥Ne is not satisfied (i.e., X<Ne), the immediately above-mentioned process of assigning I+X to M (Step S134 in FIG. 17) is only performed, and then the routine returns to a process of FIG. 16 (refer to Step S118: NO in FIG. 16→Connection symbol "C4"→Step S134 in FIG. 17→Connection symbol "C6").

As for the rest, as it is understood from steps that follow the above Connection symbol "C6" in FIG. 16, the process of Step S113 and subsequent steps of FIG. 16 will be performed as described above.

The process according to FIGS. 16 and 17 has the following implications.

The implications of this process are, briefly, to reconfirm whether there is an epoch to be determined as arousal that has been overlooked. In other words, the process supplements the above process according to FIGS. 11 and 12. In finding out whether there is any such epoch that has been overlooked, the continuous arousal X particularly plays a significant role (refer to Step S118 in FIG. 16). Specifically, if this continuous arousal X has a value equal to or greater than a certain value Ne, it is strongly presumable that a human subject was actually in an aroused state in a period around that time. Accordingly, in Step S118 and in the subsequent steps, a value of Stage is checked for each of an epoch that is earlier by O from I and an epoch that is later by O from I+X, and in a case in which the checked value is Wake, the epochs therebetween are reassigned as Stage[x]=1 even if Stage[x] was initially assigned as 0. This reassignment of the intermediate epochs is based on the above presumption.

Furthermore and more specifically, the process according to FIGS. 16 and 17 can be regarded as having two types of processes, similarly to the process according to FIGS. 11 and 12.

The first type of process is a process from Steps S119 to S125 in FIG. 16. In this process, it is determined whether there was any arousal at a point in time that is earlier in time with reference to I as of the start of arousal (performing determination at "a point in time that is earlier in time" means that, in the first type of process, the determination is performed with reference to I as I–O, I–(O–1), I–(O–2), . . . ). Furthermore, the criteria for determination is simply Stage[I–O]=Wake (refer to Step S120 in FIG. 16). As long as this is satisfied, "Wake" is assigned to Stage[x] that has the above array number.

On the other hand, the second type of process is a process from Step S126 to S133 in FIG. 16. In this process, it is determined whether there was any arousal at a point in time that is later in time with reference to [(I as of the start of arousal)+(X as of the continuous arousal)] (performing determination at "a point in time that is later in time" means, in this second type of process, this determination is performed, with reference to (I+X) as I+X+O, I+X+(O–1), I+X+(O–2), . . . ). The criteria for determination is the same as that used for the first-type process (refer to Step S128 in FIG. 17).

By performing a process according to FIGS. 16 and 17, even if supposedly, in FIG. 11 and FIG. 12, an epoch to be determined as arousal was overlooked, the epoch can be redefined as an aroused state (i.e., a type of back up is performed).

Figure 20:
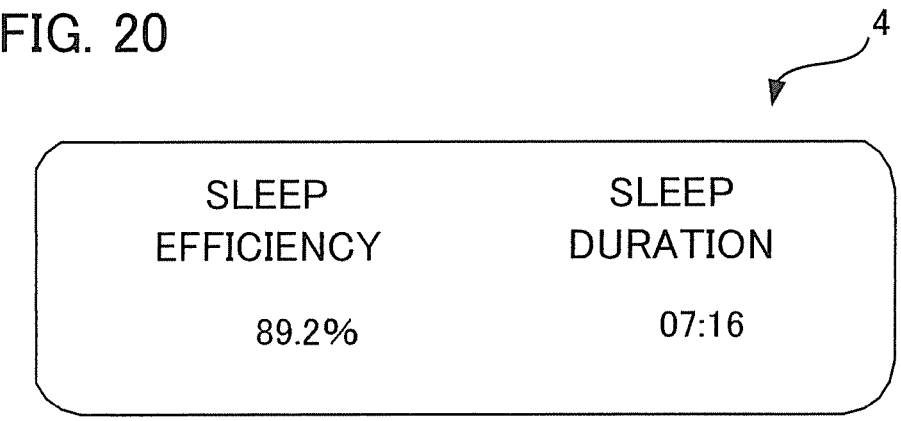
FIG. 20 is a diagram showing a first display example that is displayed as a data analysis result of Step S11 of FIG. 3.
Figure 21:
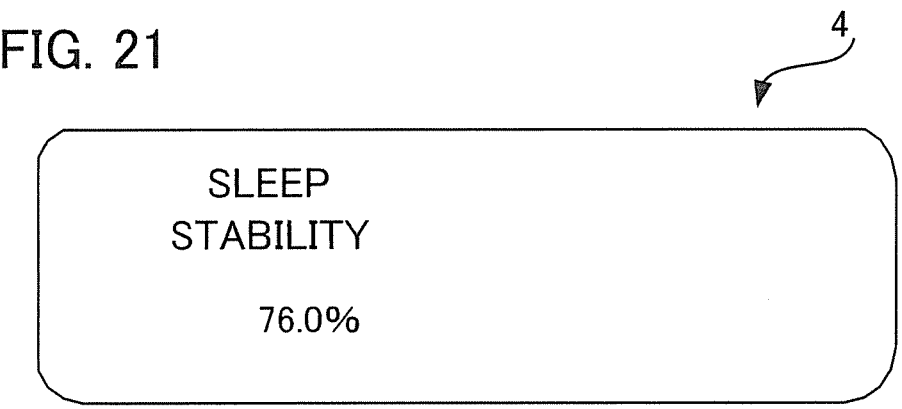
FIG. 21 is a diagram showing a second display example that is displayed as a data analysis result of Step S11 of FIG. 3.

The description that has been given so far with reference to the drawings from FIGS. 4 to 19 is the details of the data analysis process in Step S11 in FIG. 3. After performing these processes, controller CP displays the results as described earlier (Step S12 in FIG. 3), the display example of which will be such as shown in FIG. 20 or FIG. 21. FIG. 20 shows an example in which display unit 4 displays a result being "sleep efficiency 89.2%, sleep duration 07:16" (i.e., 7 hours and 16 minutes). FIG. 21 shows an example in which display unit 4 displays "sleep stability 76.0%". The "sleep efficiency" shows a percentage of 0 from among the values of Stage[x] 1, 0, 1, 0, 1, 1, 0, . . . , 1, 1 that have been set by performing each process of FIGS. 11 and 12, or FIGS. 16 and 17 described above. Furthermore, "sleep stability" is a value of "Percent" shown in FIG. 7.

Figure 22:
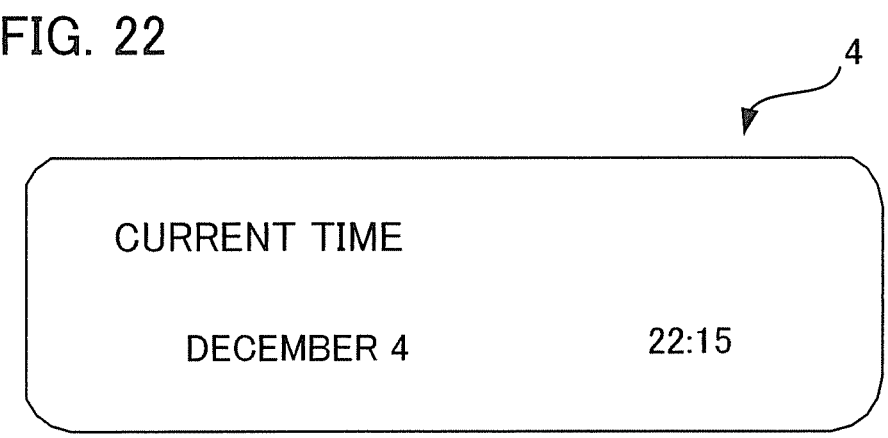
FIG. 22 is a diagram showing a display example in a normal state to be compared with FIGS. 20 and 21.

FIG. 22 is the details of what is displayed in a normal state so that it can be compared with what are shown in FIGS. 20 and 21. This corresponds to a result of a display process of a current time in Step S2 of FIG. 3.

According to sleep evaluation device 1 of the present embodiment, the following effects are attainable.

(1) Sleep evaluation device 1 of the present embodiment, as described above, Hensa[x] or HenAv[x] that is data obtained by simply carrying out addition, subtraction, multiplication, and division on body movement data D[0], D[1], . . . , and D[99] is used to determine a sleep state of a human subject. Therefore, no complicated configuration or process is required. Furthermore, while retaining such ease, Hensa[x] and HenAv[x] are different in characteristics in that Hensa[x] appropriately represents changes in body movement of a human subject in a relatively short period and that HenAv[x] appropriately represents changes in body movement of a human subject in a relatively long period. Therefore, by using Hensa[x] and HenAv[x], the determination of a sleep state of a human subject can be performed properly to a certain degree.

In summary, according to the present embodiment, the understanding of sleep states of a human subject is enabled at low cost, with an easy method, and at a degree of accuracy that is as high as possible.

(2) In sleep evaluation device 1 of the present embodiment, the baseline value, Baseline, plays a relatively significant role in determining a sleep state of a human subject. That is, the baseline value, Baseline, plays a significant role in FIG. 8 (the out-of-bed epoch calculation process), FIGS. 11 and 12 (the mid-arousal epoch calculation process), and a variable, Move, too, in particular, used in the process of FIGS. 11 and 12 is determined directly on the basis of the baseline value, Baseline (refer to FIG. 7).

Furthermore, considering that some processes other than a process in which the baseline value, Baseline, is directly used (hereinafter referred to as "a direct usage process") are performed on the premise of the direct usage process, one can say that these other processes indirectly receive benefits of the baseline value, Baseline. For example, in a case in which a given Stage[a] results in having Wake in the process in FIGS. 11 and 12, the Stage[a] could be a new initiation point in the process in FIGS. 16 and 17 (for example, refer to Step S120 or Step S128).

Thus, in the present embodiment, introducing the baseline value, Baseline, considerably increased the probability of performing the more accurate determination of a sleep state of a human subject.

Furthermore, in the present embodiment, since the baseline value, Baseline, itself is set by using a moving average value of HenAv[x] (refer to FIGS. 4 and 6 and the description thereof), the accuracy of determining a sleep state of a human subject is further enhanced.

In the foregoing, description has been given of an embodiment according to the present invention; however, a sleep evaluation device according to the present invention is not limited to the above embodiment, and the following various modifications are possible.

(1) In the above embodiment, a description was given of an example in which 100 pieces of body movement data are obtained, but the present invention is not limited thereto. It is rather more natural to assume that the number of body movement data is usually greater or is much greater than 100 ("100 pieces" in the above description was selected merely for simplicity, and not for any other purpose). Furthermore, similarly, Hensa[x] is obtained as the standard deviation of how many pieces of body movement data or HenAv[x] is obtained as the average value of how many pieces of Hensa[x] is a matter that can be basically freely set.

Furthermore, similarly, although in the above embodiment, body movement data in a digital form is obtained by performing an AD conversion on signals supplied from sensor unit 2, the length of sampling intervals in the AD conversion can be set basically freely. However, if this sampling interval is set to be relatively long, the total number of pieces of body movement data is likely to decrease, and if it is set short, the total number pieces of body movement data is likely to increase. (The term "likely" is used because the duration of remaining on the bedding usually depends on a human subject and varies daily even for the same human subject, etc.).

(2) In the above embodiment, body movement data D[x], Stage[x], Hensa[x], and HenAv[x] are all recorded in memory storage device 20 of sleep evaluation device 1, but the present invention is not limited thereto. This record can be performed, for example, in a storage medium in an external memory storage device through an appropriate interface.

(3) The sleep evaluation device according to the present invention has a main function of determining a sleep state and an aroused state of a human subject by passively receiving body movements of the human subject, and performing some type of interpretation of the body movements; however, as additional functions, a function for forcibly waking a human subject, for example, i.e., a function as an alarm clock, may be provided in an embodiment. Given that sleep evaluation device 1 of the above embodiment has a time keeping function (refer to time keeping unit 11 in FIG. 2), achieving this function as an alarm clock should be extremely easy. Such an embodiment is, of course, within the scope of the present invention.

What is claimed is:

1. A sleep evaluation device comprising:
   a body movement detector that constantly detects body movements of a human subject lying on bedding; and a determiner configured to:
   quantify at a predetermined time interval, the results of the detection of the body movement detector as N number of body movement data, in which N is a positive integral number satisfying N≥2,
   obtain G number of standard deviations for each of G groups dividing the N number of body movement data and for each body movement data included in each group, in which the G is an integral number satisfying 2≤G<N,
   obtain L number of average values of standard deviations on the basis of consecutive gs number of standard deviations (gs<G), from among the G number of standard deviations, in which L is an integral number satisfying 2≤L≤G, and wherein obtaining comprises calculating the L number of average values of standard deviations for a consecutive time interval of body movement data, and wherein each of the L number of average values of standard deviations is assigned a number, pth, which corresponds to a time of acquiring the body movement data;
   obtain as a baseline value, from among the L number of average values of standard deviations, an average value of all pth average values of standard deviations that satisfy a condition that an absolute value of a difference between a pth average value of standard deviations and a (p+1)th average value of standard deviations is equal to or is less than a predetermined value, in which p is an integral number satisfying p≤L−1, and
   determine on the basis of the G number of standard deviations and the base line baseline values, whether the human subject is in a sleep state or is in an aroused state.

2. A sleep evaluation device according to claim 1, wherein the determiner is further configured to obtain the L number of average values of standard deviations as a moving average value of the gs number of standard deviations.

3. A sleep evaluation device according to claim 1, wherein the determiner is further configured to determine, in a case in which any one of the G number of standard deviations falls below a predetermined value E, that the human subject was in an aroused state at a point in time at which a result of detection was obtained, on the basis of which result of the detection body movement data was obtained and on the basis of which body movement data the standard deviation that has fallen below the predetermined value E was calculated.

4. A sleep evaluation device according to claim 1, wherein the determiner is further configured to determine, in a case in which, from among the G number of standard deviations, a (q+1)th standard deviation is greater than a value obtained by adding a predetermined value F1 to a qth standard deviation, that the human subject was in an aroused state at a point in time at which a result of detection was obtained, on the basis of which result of detection body movement data was obtained and on the basis of which body movement data the (q+1)th standard deviation was calculated, in which q is an integral number satisfying q≤G−1.

5. A sleep evaluation device according to claim 1, wherein the determiner is further configured to determine, in a case in which any one of the G number of standard deviations is greater than a predetermined value F2, that the human subject was in an aroused state at a point in time at which a result of detection was obtained, on the basis of which result of detection the body movement data was obtained and on the basis of which body movement data the standard deviation was calculated.

6. A sleep evaluation device according to claim 1, wherein the determiner is further configured to obtain a standard deviation of the G number of standard deviations as an overall standard deviation,
   wherein the determiner is further configured to obtain an index showing the quantity of body movements of the human subject by subtracting the baseline value from an average value of G number of standard deviations and by dividing a resulting value of the subtraction by the overall standard deviation, and
   wherein the determiner is further configured to determine a point in time at which a transition from a sleep state to an aroused state has taken place on the basis of the index showing the quantity of body movements of the human subject.

7. A sleep evaluation device according to claim 1, wherein the body movement detector includes a mattress containing a predetermined fluid and detects body movements of the human subject depending on changes in pressure of the fluid.

* * * * *